(12) United States Patent
Sabourault et al.

(10) Patent No.: US 9,382,247 B2
(45) Date of Patent: Jul. 5, 2016

(54) SALTS AND PHARMACEUTICAL COMPOSITIONS THEREOF FOR THE TREATMENT OF INFLAMMATORY DISORDERS

(71) Applicant: GALAPAGOS NV, Mechelen (BE)

(72) Inventors: Nicolas Luc Sabourault, Romainville (FR); Carla De Faveri, Padua (IT); Ahmad Sheikh, North Chicago, IL (US)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 14/614,396

(22) Filed: Feb. 4, 2015

(65) Prior Publication Data
US 2015/0225398 A1 Aug. 13, 2015

(30) Foreign Application Priority Data

Feb. 7, 2014 (GB) .................................. 1402071.3

(51) Int. Cl.
| | |
|---|---|
| *C07D 471/04* | (2006.01) |
| *A61K 31/437* | (2006.01) |
| *A61K 31/541* | (2006.01) |

(52) U.S. Cl.
CPC ............ *C07D 471/04* (2013.01); *A61K 31/437* (2013.01); *A61K 31/541* (2013.01); *C07B 2200/13* (2013.01)

(58) Field of Classification Search
CPC ... C07D 471/04; A61K 31/437; A61K 31/541
USPC ....................... 544/58.2; 514/228.5
See application file for complete search history.

(56) References Cited

U.S. PATENT DOCUMENTS 8,088,764 B2 * 1/2012 Menet .................. C07D 471/04
514/228.5

FOREIGN PATENT DOCUMENTS

WO WO2010149769 12/2010

OTHER PUBLICATIONS

Foreign priority document GB1402071.3, filed Feb. 7, 2014.*
Kopf et al., Averting inflammation by targeting the cytokine environment Nature Reviews, Drug Discovery, vol. 9, Sep. 2010, 703-718.
Mullighan, et al., JAK mutations in high-risk childhood acute lymphoblastic leukemia, PNAS, 2009, 106(23), 9414-18.
O'Sullivan et al., Cytokine receptor signaling through the Jak-Stat-Socs pathway in disease, Molecular Immunology 44 (2007) 2497-2506.
Vainchenker et al., JAKs in pathology: Role of Janus kinases in hematopoietic malignancies and immunodeficiencies, Seminars in Cell & Developmental Biology, 2008, 19, 385¿ 393.
Xiang et al., Identification of somatic JAK1 mutations in patients with acute myeloid leukemia, Blood, 2008, 111: 4809-4812.
Zikherman et al., Unraveling the functional implications of GWAS: how T cell protein tyrosine phosphatase drives autoimmune disease, J Clin Invest., 2011, 121(12), 4618-4621.
Zenz et al, Psoriasis-like skin disease and arthritis caused by inducible epidermal deletion of Jun proteins, Nature, 2005, 437, 369-375.
Dolgin, Elie, Companies hope for kinase inhibitor JAKpot, Nature Reviews Drug Discovery, Oct. 2011, 10, 717-718.
Punwani et al., Preliminary clinical activity of a topical JAK1/2 inhibitor in the treatment of psoriasis, J Am Acad Dermatol, 2012, 67(4), 658-64.
Ingersoll et al., The impact of medication regimen factors on adherence to chronic treatment: a review of literature, J Behav Med., Jun. 2008, 31(3), 213-224.
Verstovsek S, Therapeutic potential of JAK2 inhibitors, Hematology Am Soc Hematol Educ Program, 2009, 636-42.
Zhang et al., Activation of Jak/STAT proteins involved in signal transduction pathway mediated by receptor for interleukin 2 in malignant T lymphocytes derived from cutaneous anaplastic large T-cell lymphoma and Sezary syndrome, Proc. Natl. Acad. Sci. USA, Aug. 1996, vol. 93, pp. 9148-9153.
Berishaj et al., Stat3 is tyrosine-phosphorylated through the interleukin-6/glycoprotein 130/Janus kinase pathway in breast cancer, Breast Cancer Res. 2007, 9(3), R32.
O'Dell, Therapeutic Strategies for Rheumatoid Arthritis;2004 N Eng J Med, 350, 2591-602.
Naka T et al., The paradigm of IL-6: from basic science to medicine. Arthritis Res,2002; 4 (suppl 3), S233-S242.
Chmp, Guideline on Clinical Investigation of Medicinal Products indicated for the treatment of Psoriasis., 2004.

(Continued)

*Primary Examiner* — Kahsay Habte
(74) *Attorney, Agent, or Firm* — Klauber & Jackson LLC

(57) ABSTRACT

The present invention discloses salts of a Compound 1:

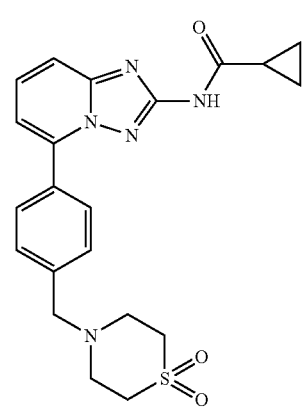

Compound 1 useful in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

2 Claims, 11 Drawing Sheets

(56) References Cited

OTHER PUBLICATIONS

Lipinski et al., Experimental and computational approaches to estimate solubility and permeability in drug discovery and development settings, Advanced Drug Discovery Reviews, 46: 3-26, (2001).

Smolen J.S. et al, Therapeutic strategies for rheumatoid arthritis, Nat Rev Drug Discov, 2003, 2(6), 473-88.

Tam et al., Expression levels of the JAK/STAT pathway in the transition from hormone-sensitive to hormone-refractory prostate cancer, British Journal of Cancer, 2007, vol. 97, 378-383.

Constantinescu et al., Mining for JAK-STAT mutations in cancer, Trends in Biochemical Sciences, vol. 33, No. 3, 122-131.

* cited by examiner

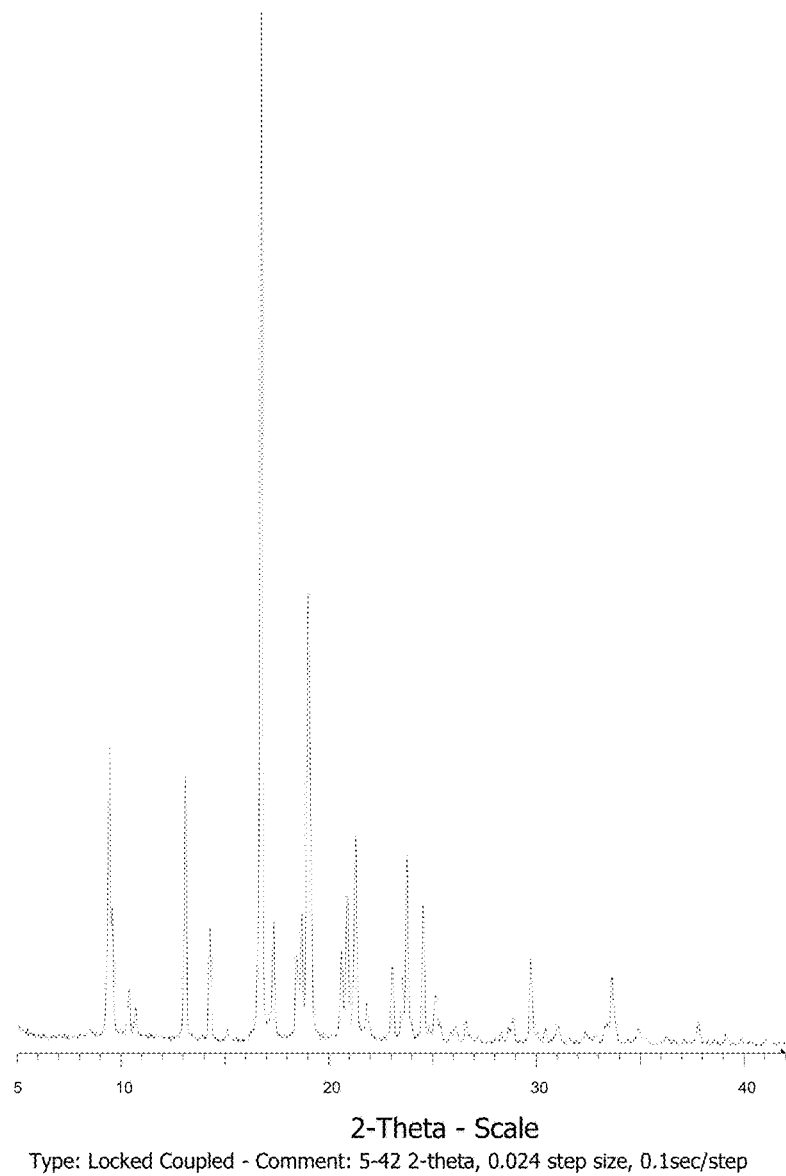
Figure 1. Compound 1 pattern 1 XRPD diffractogram

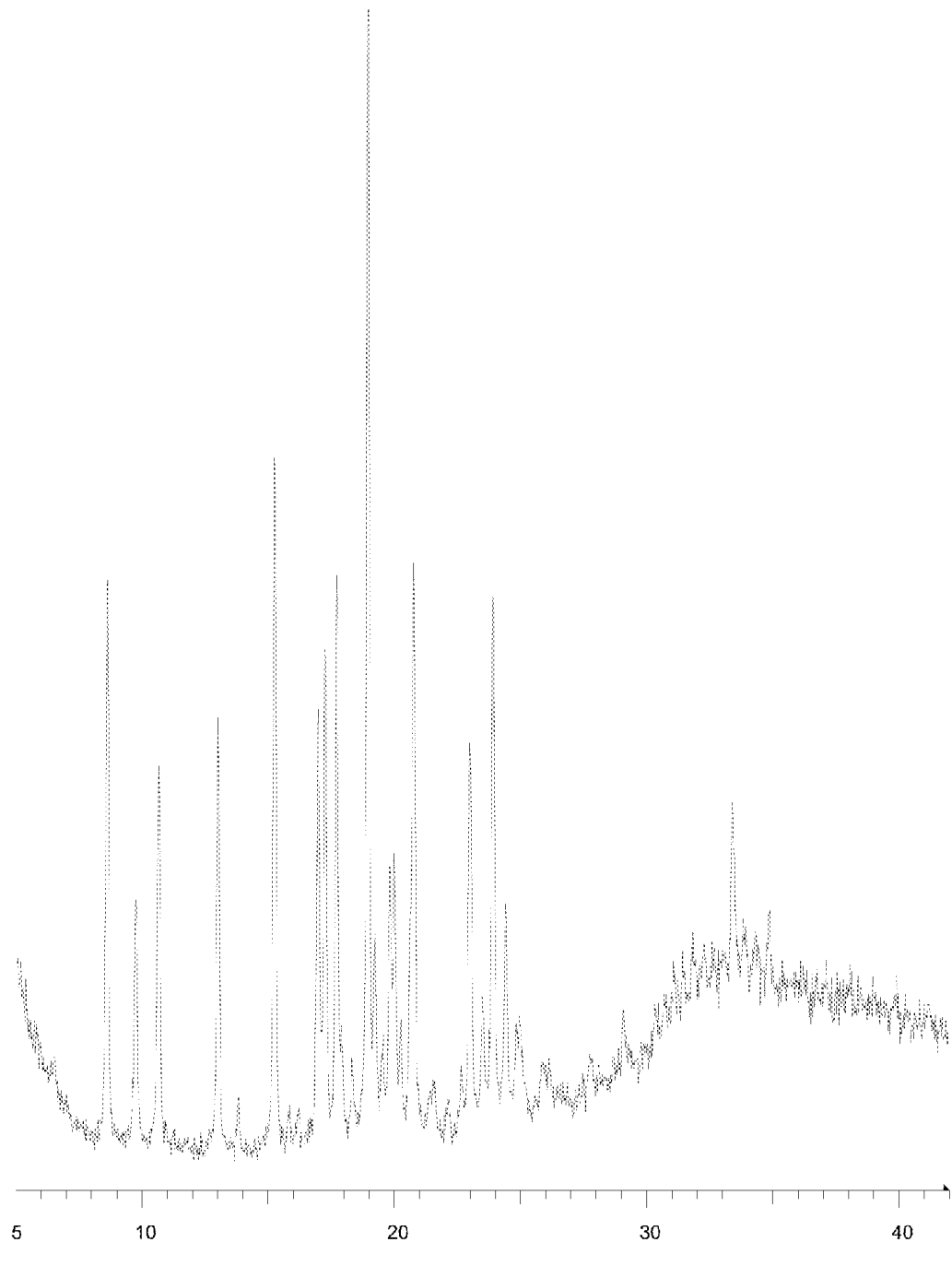
Figure 2. Compound 1 pattern 3 XRPD diffractogram

Figure 3. Compound 1 pattern 4 XRPD diffractogram
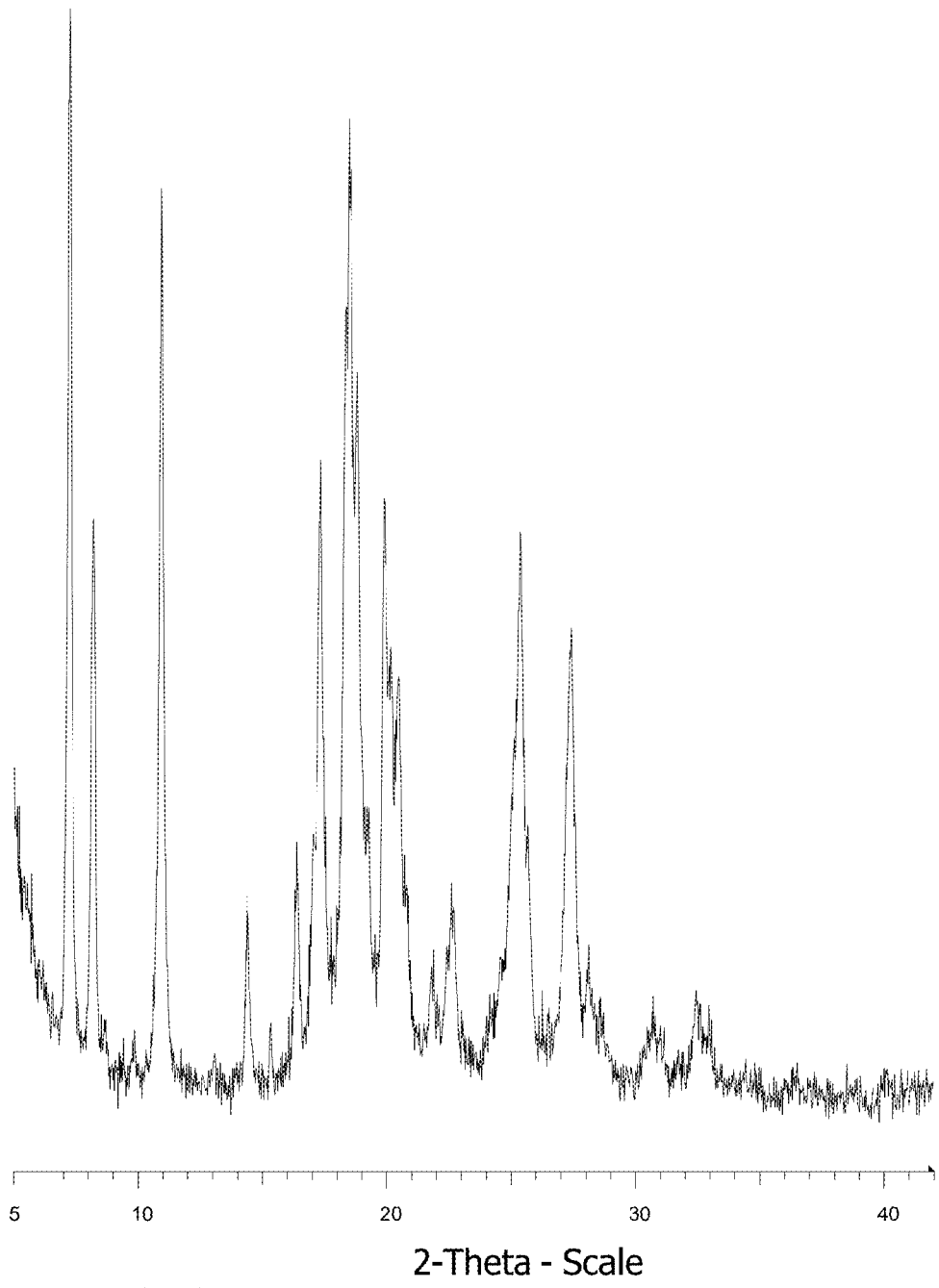

Figure 4. Compound 1. HCl XRPD diffractogram
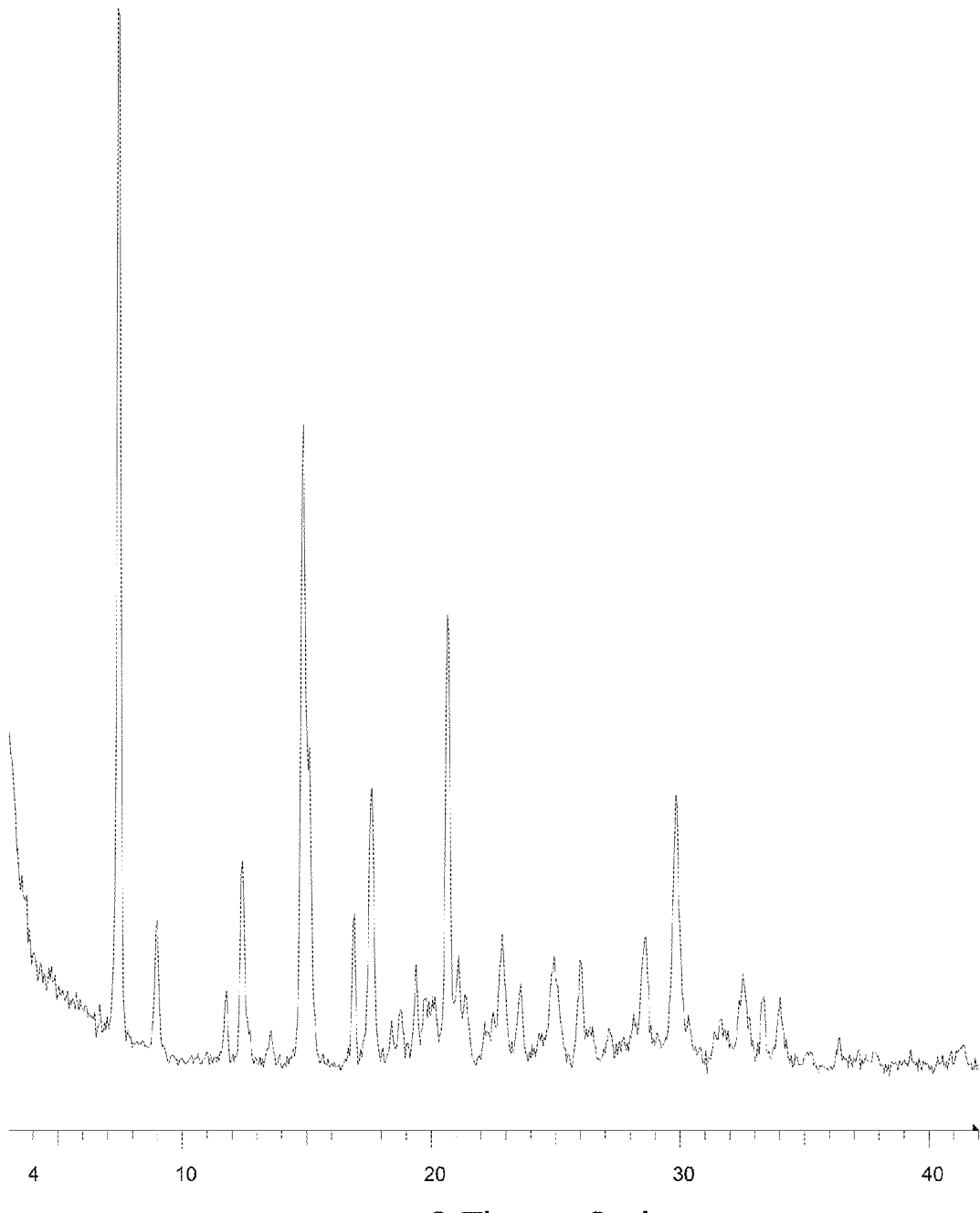
2-Theta - Scale
2-42 degrees; 0.05 step size; 0.5 sec/step - Humidity: n.a.

Figure 5. Compound 1. HCl.3H$_2$O XRPD diffractogram
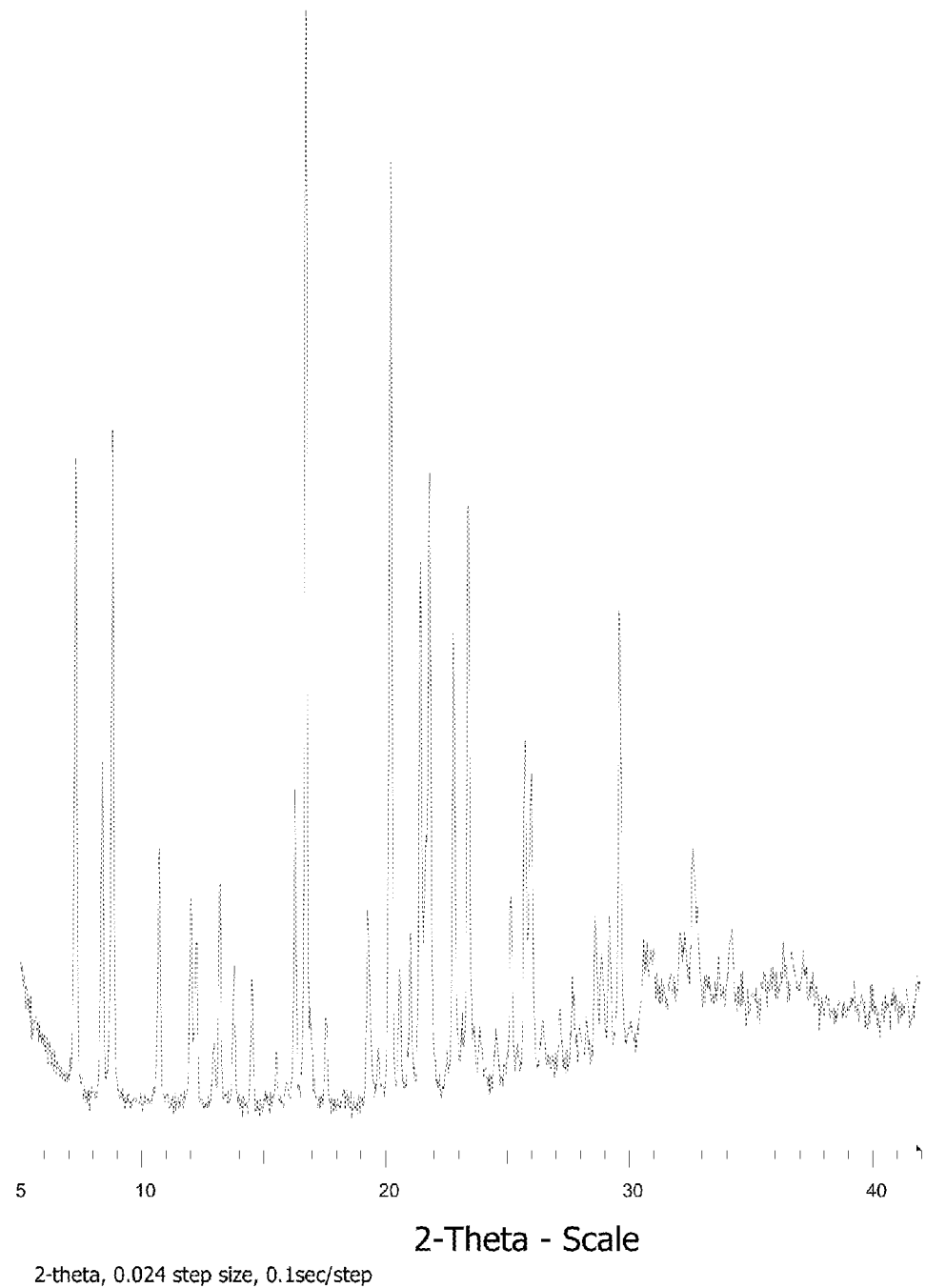

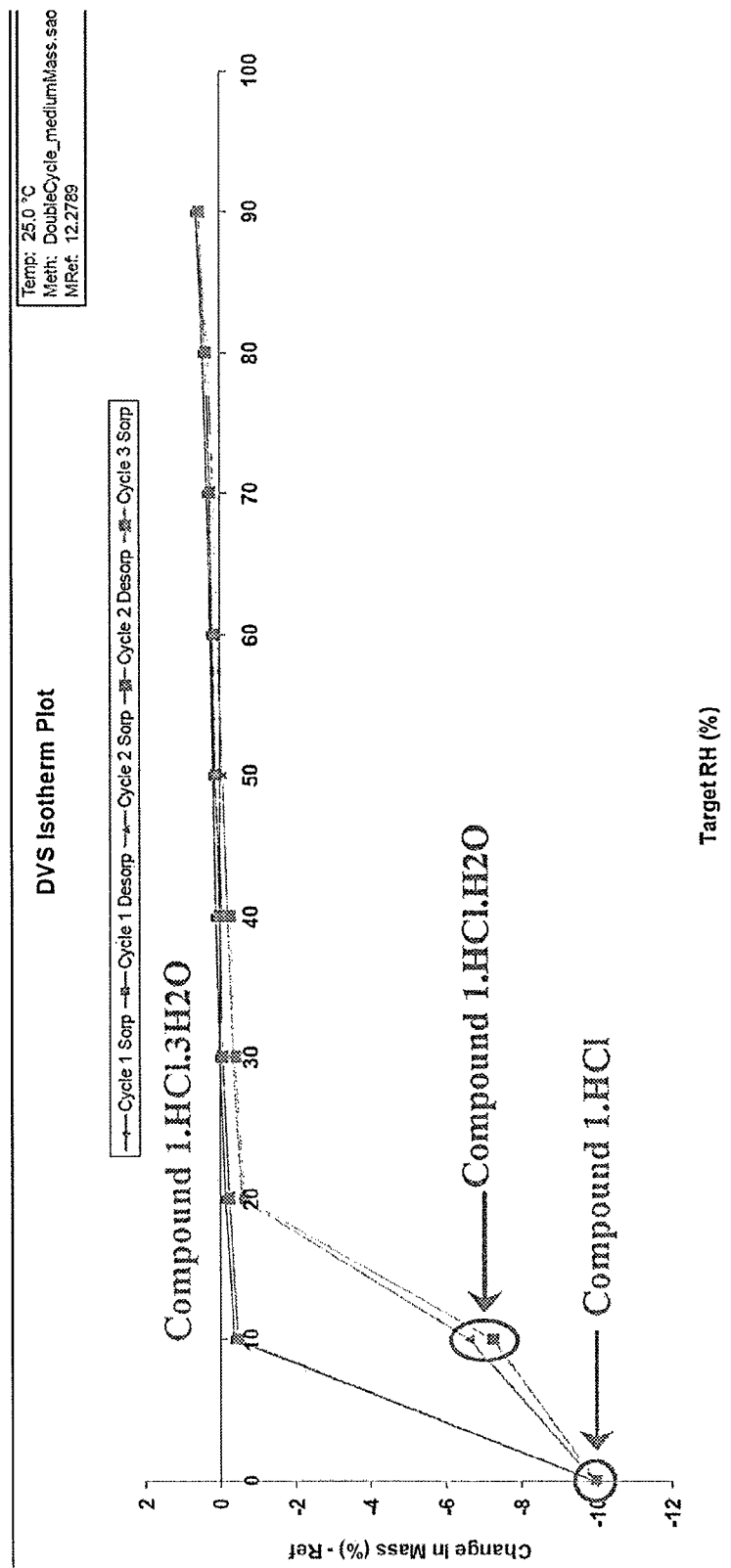
Figure 6. Compound 1. HCl.3H₂O Pattern 4 DVS analysis

Figure 7. Compound 1. HCl3H$_2$O DSC trace
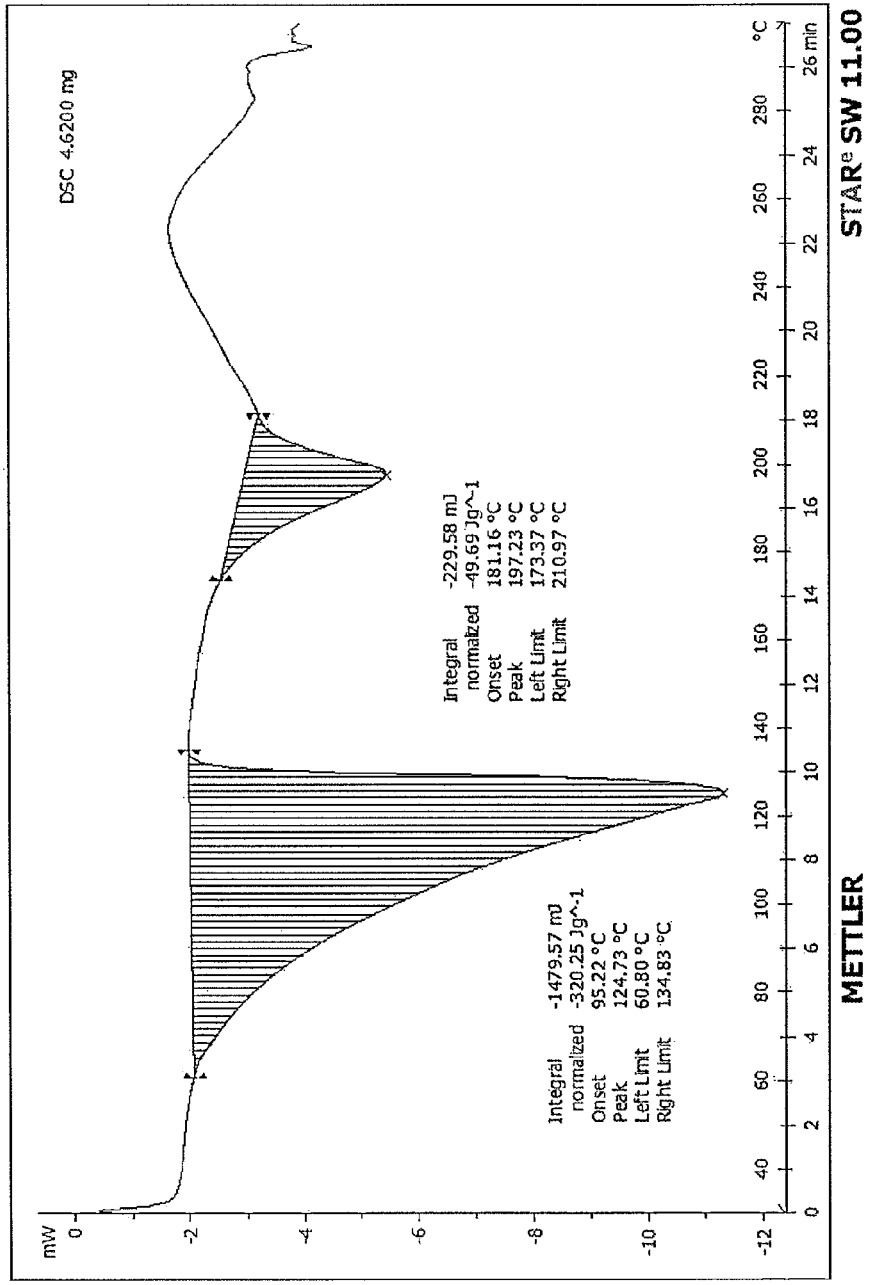

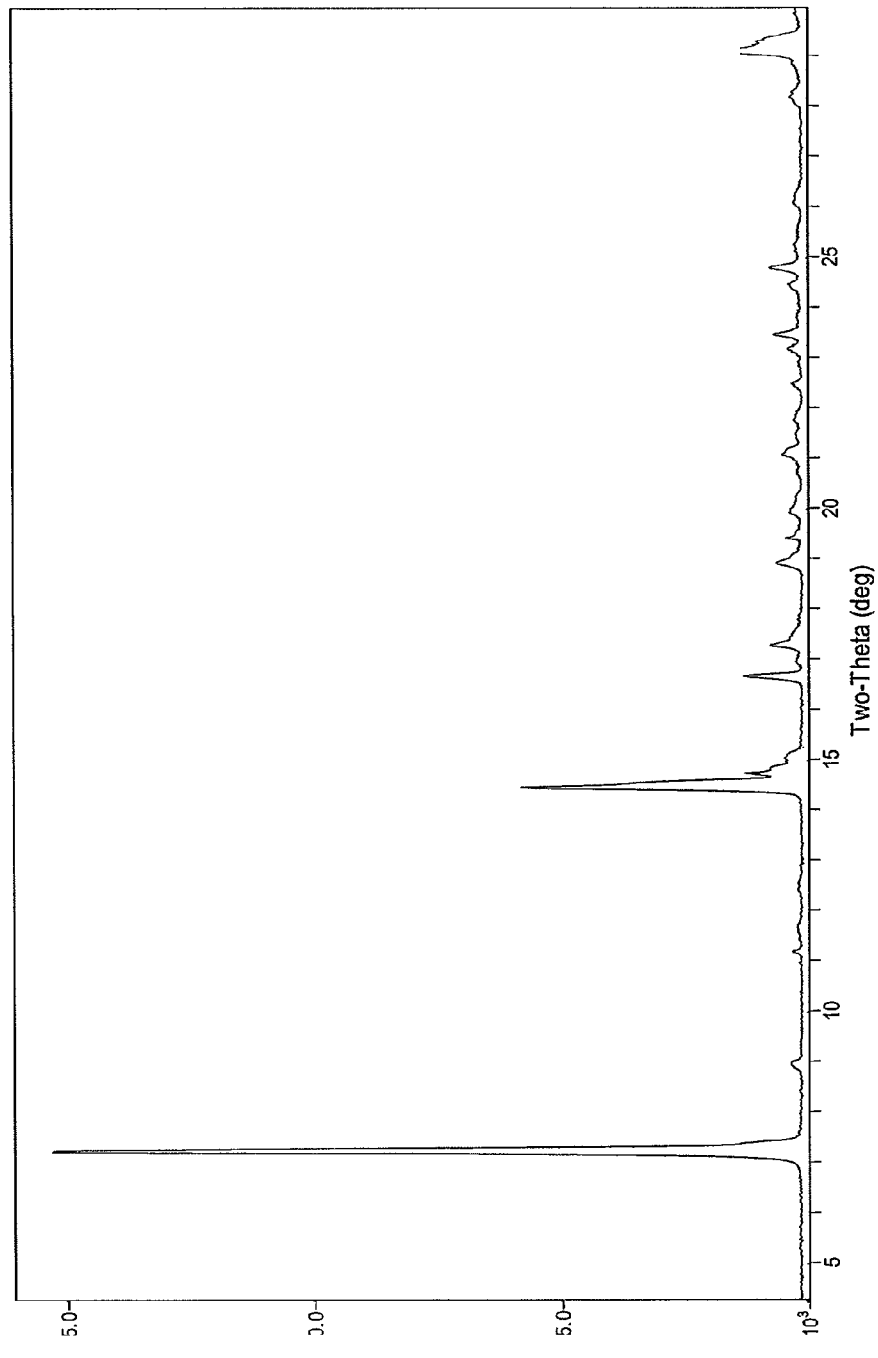
Figure 8. Compound 1. HCl. MeOH XRPD diffractogram

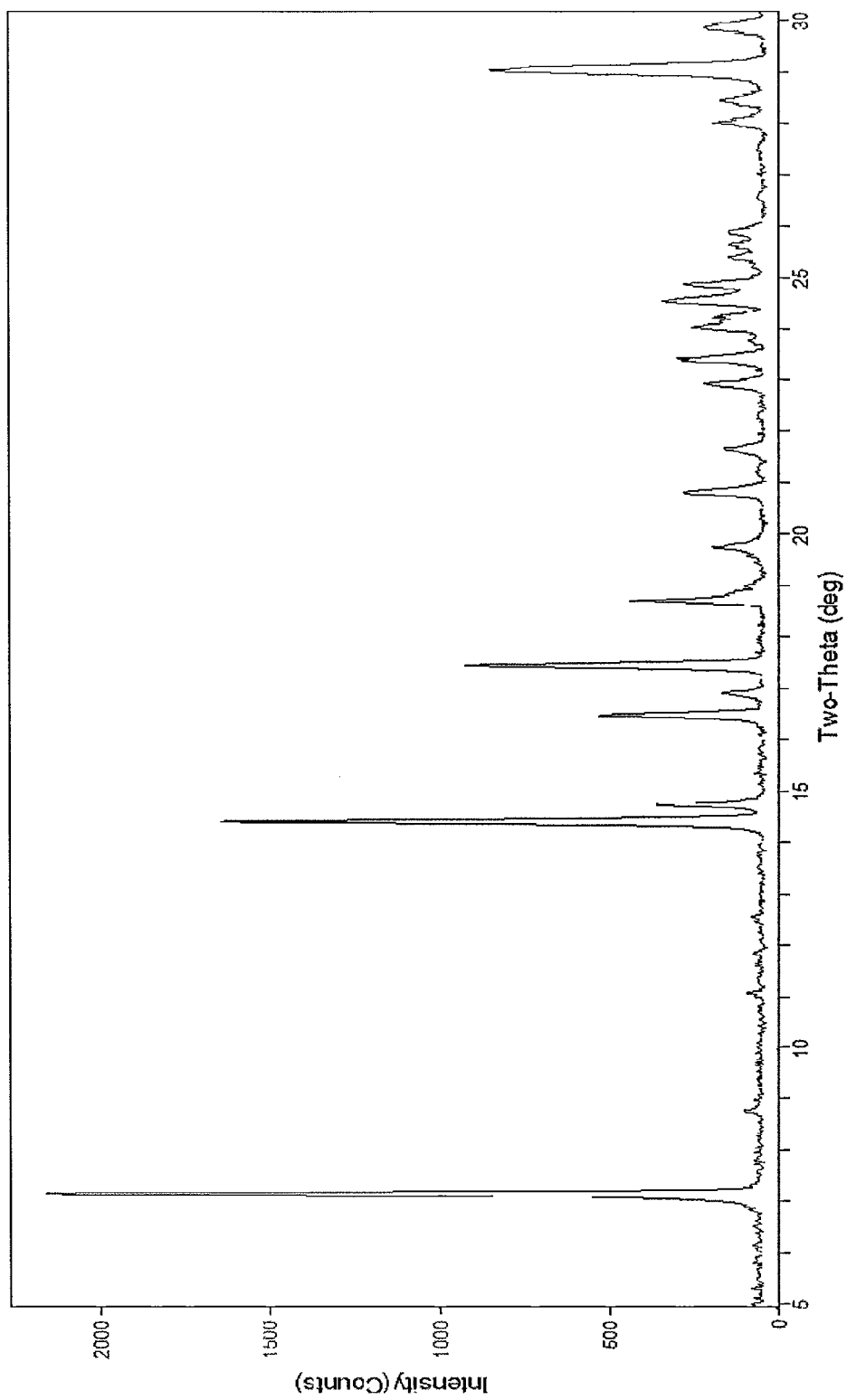
Figure 9. Compound 1. HCl.1.5 HCO₂H XRPD diffractogram

Figure 10. Compound 1 AUC values following once daily p.o. dosing.
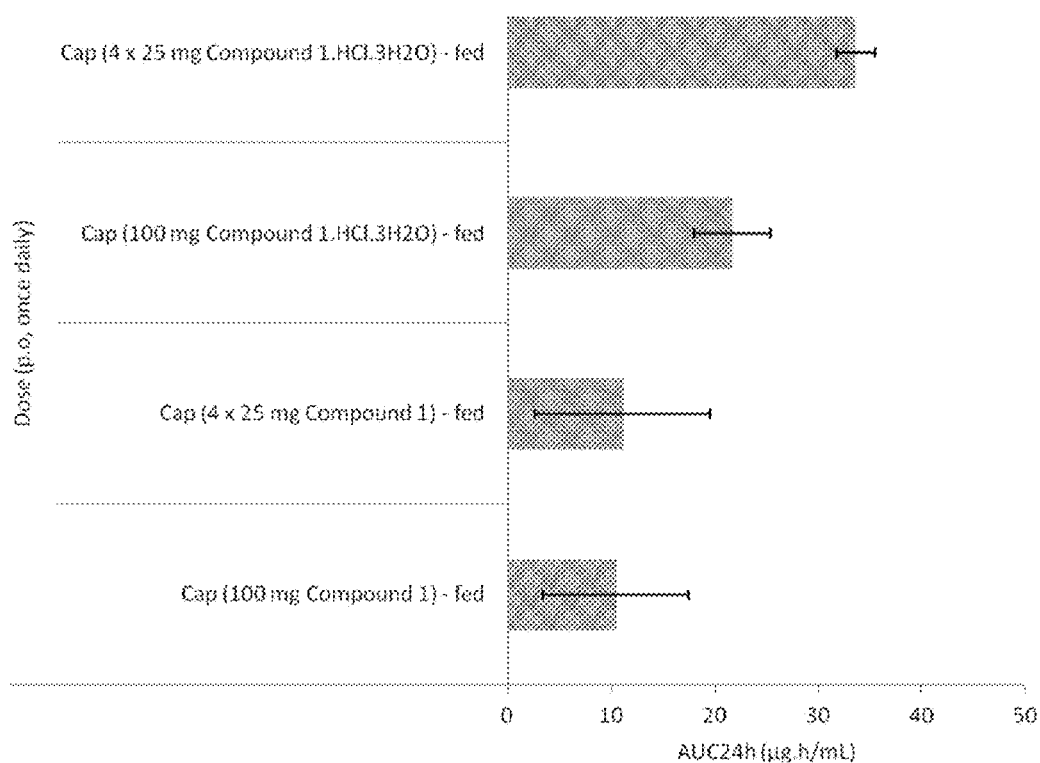

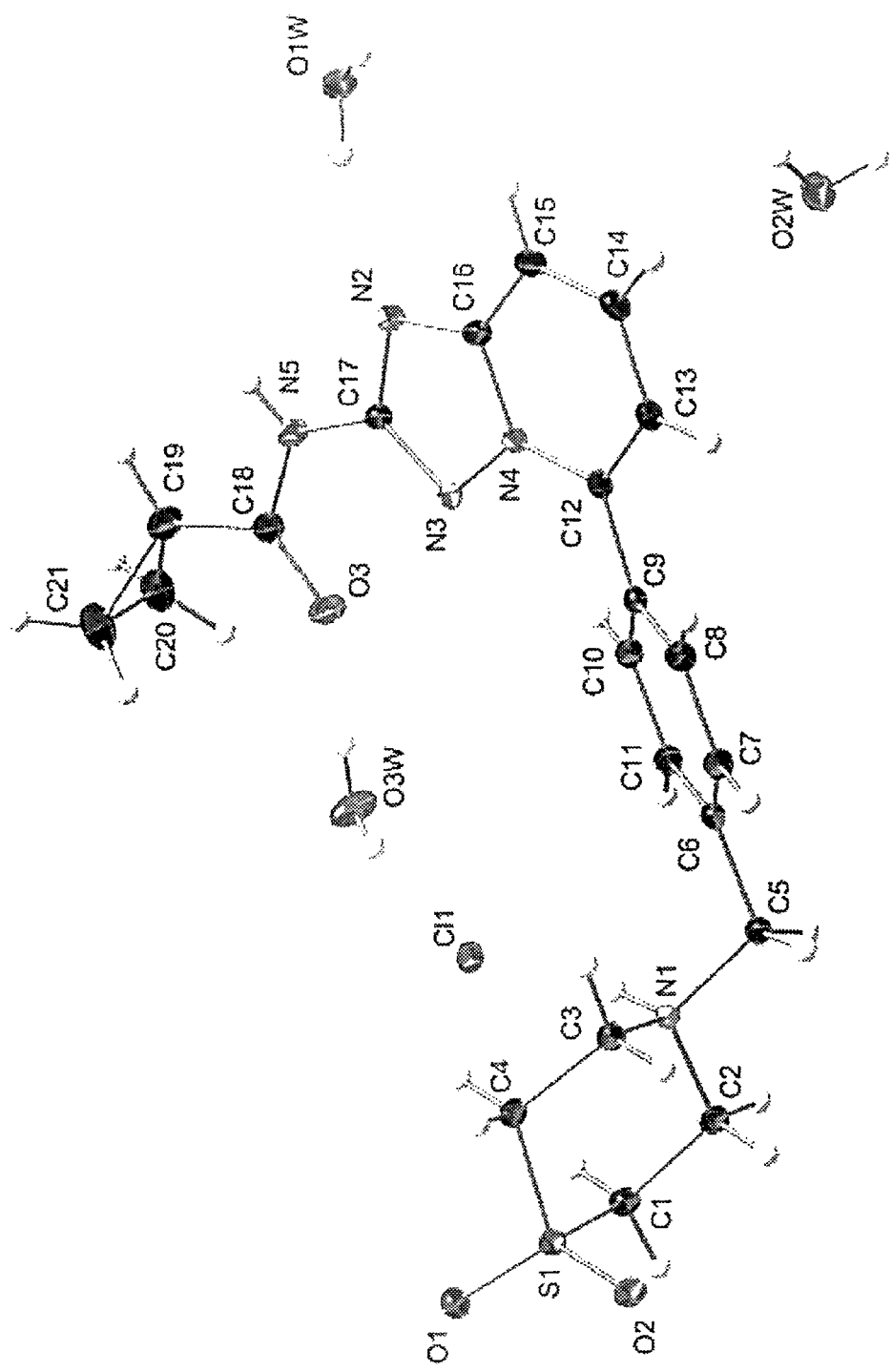
Figure 11. Compound1.HCl.3H₂O Crystal Structure.

SALTS AND PHARMACEUTICAL COMPOSITIONS THEREOF FOR THE TREATMENT OF INFLAMMATORY DISORDERS

CROSS REFERENCE TO RELATED APPLICATION

The present application claims the priority of co-pending United Kingdom Application No. GB1402071.3 filed on Feb. 7, 2014, and the disclosure of said application is incorporated herein by reference in its entirety. Applicants claim the benefits of said application under 35 U.S.C. §119.

FIELD OF THE INVENTION

The present invention relates to the salt and crystalline forms of a compound according to Formula I, useful in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons. In particular, the salt of the invention inhibits JAK, a family of tyrosine kinases, and more particularly JAK1. The present invention also provides pharmaceutical compositions comprising the salt of the invention and methods for the prophylaxis and/or treatment of diseases including inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons by administering a salt of the invention according to Formula I.

BACKGROUND OF THE INVENTION

Current therapies for treating inflammatory conditions, autoimmune diseases, proliferative diseases, allergy, transplant rejection, diseases involving impairment of cartilage turnover, congenital cartilage malformations, and/or diseases associated with hypersecretion of IL6 or interferons, in particular rheumatoid arthritis, are far from satisfactory and there remains a need to identify new therapeutic agents that may be of use in their treatment. These conditions are chronic conditions which require long term therapy, and repeated intake of the drug. Long term treatment might be a heavy burden on the patient and the practitioner alike, since the patient might be or become intolerant to the drug, and furthermore high dosage, or high dosage frequency may result in uncomfortable side effects, and/or low patient compliance, where the patient may occasionally, deliberately or accidentally, miss a dose. The impact of non-adherence varies across chronic illnesses, and ranges from minimal to very significant (Ingersoll & Cohen, 2008). Therefore, there is a need to identify new agents to reinforce the arsenal of the practitioner, and compounds with low frequency dosage regimen to improve the life of the patients.

Janus kinases (JAKs) are cytoplasmic tyrosine kinases that transduce cytokine signaling from membrane receptors to STAT transcription factors. Four JAK family members are described, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF and PRL (Vainchenker, Dusa, & Constantinescu, 2008).

The combination of genetic models and small molecule JAK inhibitor research revealed the therapeutic potential of several JAKs.

JAK1 is a target in the immuno-inflammatory disease area. JAK1 heterodimerizes with the other JAKs to transduce cytokine-driven pro-inflammatory signaling. Therefore, inhibition of JAK1 is of interest for immuno-inflammatory diseases with pathology-associated cytokines that use JAK1 signaling, such as IL-2, IL-6, IL-4, IL-5, IL-13, or IFNgamma, as well as for other diseases driven by JAK-mediated signal transduction.

In the JAK family members' roles, some overlap exists, since most signaling pathways involve more than one JAK, however for some growth factors such as erythropoietin and thrombopoietin, only JAK2 is involved.

JAK3 plays a major role in blocking immune function via transmission of signals generated by interleukin (IL)-2.

On the other hand, TYK2 would appear to work in combination with JAK2 in order to transduce signaling of cytokines such as IL-12 and IL-23.

The role of JAK enzymes has been mostly studied using mice where each of the JAK family members has been deleted. JAK1 knockout mice exhibit a perinatal lethal phenotype and also have defective lymphoid development and function as a result of defective signaling by cytokines through JAK1. JAK2 deficiency results in embryonic lethality at day 12 as a result of a failure in definitive erythropoiesis. JAK3-deficient mice have severe combined immunodeficiency (SCID) phenotype but do not have non-immune defects (Verstovsek, 2009).

As has been observed with pan JAK inhibitors, non-selective inhibition may be linked to side effects such as anemia, an increased rate of infections, lower neutrophil and lymphocyte counts, a decrease in haemoglobin, and elevated cholesterol levels (Dolgin, 2011).

Therefore, the development of a selective JAK inhibitor would be beneficial in order to minimize such side effects.

The degeneration of cartilage is the hallmark of various diseases, among which rheumatoid arthritis and osteoarthritis are the most prominent. Rheumatoid arthritis (RA) is a chronic joint degenerative disease, characterized by inflammation and destruction of the joint structures. When the disease is untreated, it can lead to substantial disability and pain due to loss of joint function and result in shortened life-expectancy. The aim of a RA therapy, therefore, is not only to slow down the disease but to attain remission in order to stop the joint destruction and improve quality of life. Besides the severity of the disease outcome, the high prevalence of RA (~0.8% of adults are affected worldwide) means a high socio-economic impact. (Smolen & Steiner, 2003) (O'Dell, 2004). JAK1 is implicated in intracellular signal transduction for many cytokines and hormones. Pathologies associated with any of these cytokines and hormones can be ameliorated by JAK1 inhibitors. Hence, several allergy, inflammation and autoimmune disorders might benefit from treatment with compounds described in this invention including rheumatoid arthritis, systemic lupus erythematosus, juvenile idiopathic arthritis, osteoarthritis, asthma, chronic obstructive pulmonary disease (COPD), tissue fibrosis, eosinophilic inflammation, eosophagitis, inflammatory bowel diseases (e.g. Crohn's disease, ulcerative colitis), transplant, graft-versus-host disease, psoriasis, myositis, psoriatic arthritis, ankylosing spondylitis, juvenile idiopathic arthritis, and multiple sclerosis. (Kopf, Bachmann, & Marsland, 2010)

Psoriasis is a disease that can affect the skin. The cause of psoriasis is not fully understood but it is believed that it is an immune mediated related disease linked to the release of cytokines, in particular TNFα, which causes inflammation and rapid reproduction of the skin cells. This hypothesis has been corroborated by the observation that immunosuppressant medication can clear psoriasis plaques. (Zenz, et al., 2005) Psoriasis can also cause inflammation of the joints, which is known as psoriatic arthritis. Between 10-30% of all people with psoriasis also have psoriatic arthritis. ((CHMP), 18 Nov. 2004) Because of its chronic recurrent nature, psoriasis is a challenge to treat. It has recently been demonstrated that inhibition of JAK could result in successful improvement of the psoriatic condition (Punwani, et al., 2012).

Inflammatory bowel disease (IBD) is a group of inflammatory conditions of the colon and small intestine. The major types of IBD are Crohn's disease and ulcerative colitis. Recently, it has been found via genome-wide association (GWAS) studies that T cell protein tyrosine phosphatise (TCPTP) is a JAK/STAT and growth factor receptor phosphatase that has been linked to the pathogenesis of type 1 diabetes, rheumatoid arthritis, and Crohn's disease by GWAS. (Zikherman & Weiss, 2011) Therefore, inhibition of the JAK pathway might provide a way of treating IBD.

JAK family members have been implicated in additional conditions including myeloproliferative disorders (O'Sullivan, Liongue, Lewis, Stephenson, & Ward, 2007), where mutations in JAK2 have been identified. This indicates that inhibitors of JAK in particular JAK2 may also be of use in the treatment of myeloproliferative disorders. Additionally, the JAK family, in particular JAK1, JAK2 and JAK3, has been linked to cancers, in particular leukaemias (e.g. acute myeloid leukaemia (O'Sullivan, Liongue, Lewis, Stephenson, & Ward, 2007) (Xiang, et al., 2008) and acute lymphoblastic leukaemia (Mullighan, 2009)), cutaneous T-cell lymphoma (Zhang, 1996) or solid tumours e.g. uterine leiomyosarcoma (Constantinescu, Girardot, & Pecquet, 2007), prostate cancer (Tam, McGlynn, Traynor, Mukherjee, Bartlett, & Edwards, 2007) and breast cancer (Berishaj, et al., 2007). These results indicate that inhibitors of JAK, in particular of JAK1, may also have utility in the treatment of cancers (leukaemias and solid tumours e.g. uterine leiomyosarcoma, prostate cancer, pancreatic cancers).

In addition, Castleman's disease, multiple myeloma, mesangial proliferative glomerulonephritis, psoriasis, and Kaposi's sarcoma are likely due to hypersecretion of the cytokine IL-6, whose biological effects are mediated by intracellular JAK-STAT signaling (Naka, Nishimoto, & Kishimoto, 2002). This result shows that inhibitors of JAK, may also find utility in the treatment of said diseases.

Thus, compounds which are potent inhibitors of JAK would offer the potential for treating a wide variety of the disease and conditions described above.

The compound cyclopropanecarboxylic acid {5-[4-(1,1-dioxo-thiomorpholin-4-ylmethyl)-phenyl]-[1,2,4]triazolo[1,5-a]pyridin-2-yl}-amide (Compound 1), which has the chemical structure:

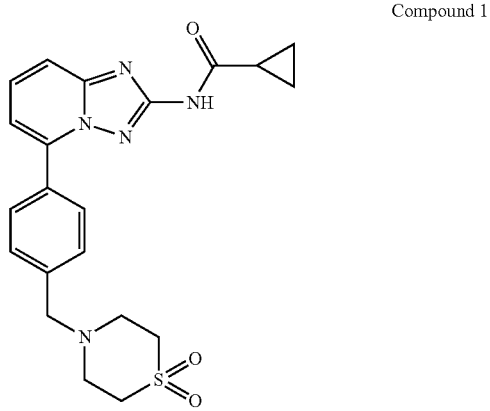 [SMILES: O=C(Nc1nc2cccc(-c3ccc(CN4CCS(=O)(=O)CC4)cc3)n2n1)C1CC1]

Compound 1 is disclosed in our earlier application WO2010/149769 (Menet C. J., 2010) as being an inhibitor of JAK and as being useful in the treatment of inflammatory conditions, autoimmune diseases, proliferative diseases, allergy, transplant rejection, diseases involving impairment of cartilage turnover, congenital cartilage malformations, and/or diseases associated with hypersecretion of IL6 or interferons. Hereafter this compound is named Compound 1. The data presented in WO 2010/149769 demonstrate that despite similar in vitro activities, Compound 1 has unexpectedly high in vivo potency compared with structurally similar compounds.

An important characteristic of various bioactive substances (for example but without limitation pharmaceuticals, medicines and biocides, usually referred to as drugs) is their "bioavailability" or active concentration in a form which can be absorbed and utilized by a target organ or organism. In many cases, the bioavailability is related to the drug solubility in water.

To be of use as a therapeutic agent, the drug should be soluble in a suitable concentration range for the required period of time. Various options are available to achieve these properties, including formulating the drug as a pill, capsules, solutions, or other similar formulations. Of particular interest are "zero-order release" drugs, in which the rate of drug release is constant. However, developing these systems can be complicated and expensive.

Often, drugs in their free base form are poorly soluble in water, but the presence of acidic sites (for example carboxylic acids, phenols, sulfonic acids) or basic sites (for example amino groups, basic nitrogen centres) can be used advantageously to produce salts of the drug. The resulting ionic compounds become much more soluble in water by virtue of their ionic character and lower dissolution energy, and thus improve bioavailability. A guideline of 50 µg/mL for aqueous solubility is provided by Lipinsky et al. (Lipinski, Lombardo, Dominy, & Feeney, 2001).

Salt forming agents are available in large number, and salt selection must be carefully designed. The aim of the salt selection is to identify the best salt form suitable for development, and is based primarily on four main criteria: aqueous solubility at various pH, high degree of crystallinity, low hygroscopicity, and optimal chemical stability (Handbook of Pharmaceutical Salts: Properties, Selection and Use, Stahl, P. H. and Wermuth, C. G. Eds. Wiley-VCH, Weinheim, Germany, 2002).

If a suitable salt of a drug can be identified, further investigations are required to identify whether there are alternative crystalline forms. The availability of such alternative forms is highly unpredictable and can require a combination of intuition, careful empirical design, perseverance and serendipity. On top of the challenges associated with even finding one or more defined crystalline forms, the properties of any crystalline forms thus discovered need to be carefully evaluated to see if one or more of them is actually suitable for pharmaceutical development. Indeed, in a first aspect, crystallinity of drugs affects, among other physical and mechanical properties, solubility, dissolution rate, flowability, hardness, compressability, and melting point. In a second aspect, a crystalline form may have advantages over the amorphous form, for example, purification to the high degree of purity required by most regulatory authorities is more efficient and therefore costs less for the crystalline form than for the amorphous solid. In addition, handling of the crystalline form is improved over the amorphous form, which tends to be oily, or sticky, and in practice, drying of a crystalline material which has a well-defined drying or desolvation temperature is more easily controlled, than for the amorphous solid which has a greater affinity for organic solvents and variable drying temperature. Finally downstream processing of the crystalline drug permits enhanced process control. In a third aspect, physical and chemical stability, and therefore shelf-life is also improved for crystalline forms over amorphous forms.

Finally, pharmacokinetic and pharmacodynamic properties of a drug may be linked to a particular crystalline structural form, and it is paramount to produce and retain the same form from production to administration to the patient. Therefore the obtention of salts, and/or crystalline forms over amorphous materials is highly desirable (Hilfiker, Blatter, & von Raumer, 2006).

Thus the object of this invention is to disclose salt forms and polymorphs of the salts of the invention, which have desirable pharmacological properties, and which are show improvements in their pharmaceutical profile compared to the free base and/or amorphous form of the salt of the invention, in particular improved in vivo exposure.

DESCRIPTION OF THE DRAWINGS

FIG. 1 shows the XRPD diffractogram of Compound 1 pattern 1.

FIG. 2 shows the XRPD diffractogram of Compound 1 pattern 3.

FIG. 3 shows the XRPD diffractogram of Compound 1 pattern 4.

FIG. 4 shows the XRPD diffractogram of Compound 1.HCl.

FIG. 5 shows the XRPD diffractogram of Compound 1.HCl.3H$_2$O.

FIG. 6 shows the Compound 1.HCl.3H$_2$O DVS analysis.

FIG. 7 shows the DSC trace of Compound 1.HCl.3H$_2$O.

FIG. 8 shows the XRPD diffractogram of Compound 1.HCl.MeOH.

FIG. 9 shows the XRPD diffractogram of Compound 1.HCl.1.5HCO$_2$H.

FIG. 10 shows the exposure of Compound 1 either as a free base or as an HCl.3H$_2$O salt upon daily po dosing.

FIG. 11 shows the Compound1.HCl.3H$_2$O crystal structure.

SUMMARY OF THE INVENTION

The present invention is based on the identification of novel salts and crystalline forms of Compound 1, useful in the treatment and/or prophylaxis of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons. In particular, the salts of the invention may act as inhibitors of JAK, and in more particularly of JAK1. The present invention also provides methods for the production of these salts, pharmaceutical compositions comprising these salts and methods for the treatment and/or prophylaxis of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons by administering the salts of the invention.

Accordingly, in one aspect the present invention provides a salt of a compound according to Formula (I) below (hereafter also named Compound 1):

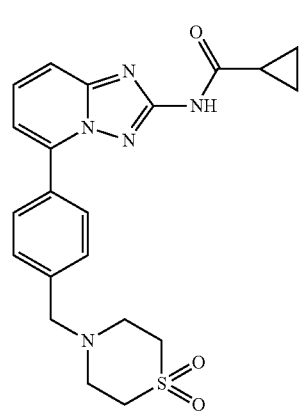

Compound 1 wherein said salt is formed with hydrobromic acid, hydrochloric acid, sulfuric acid, toluenesulfonic acid, benzenesulfonic acid, oxalic acid, maleic acid, naphthalene-2-sulfonic acid, naphthalene-1,5-disulfonic acid, 1-2-ethane disulfonic acid, methanesulfonic acid, 2-hydroxy ethanesulfonic acid, phosphoric acid, ethane sulfonic acid, malonic acid, 2-5-dihydroxybenzoic acid, or L-Tartaric acid.

Accordingly, in one aspect the present invention provides a salt of a compound according to Formula (I) below (hereafter also named Compound 1):

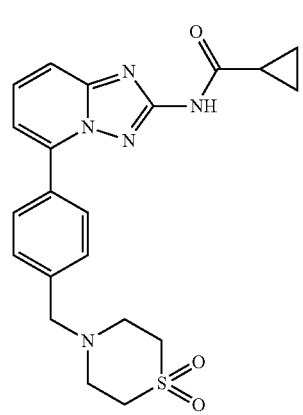

Compound 1 wherein said salt is formed with hydrochloric acid

In another aspect of the invention, the salt of the invention is a [Compound 1.HCl.3H$_2$O] adduct in a solid crystalline form, wherein the crystalline form is characterized at least by a powder X-ray diffraction peak at any one or more of the following positions: 7.3, 8.4, 8.8, 10.7, 12.0, 12.2, 13.2, 13.7, 14.5, 16.3, 16.7, 17.6, 19.3, 20.2, 20.6, 21.0, 21.4, 21.8, 22.8, 23.4, 23.9, 24.5, 25.2, 25.7, 25.9, 26.4, 27.2, 27.7, 28.3, 28.6, 28.9, 29.2, 29.6, 7 and 32.7° 2θ±0.2° 2θ.

In a particular aspect of the invention, the salt of the invention exhibits improved solubility and exposure over the free base, which may result in an improved efficacy and a drug's lower dosage being administered. In turn, lowering the drug dosage level may potentially lower toxicity that may occur via drug-drug interaction.

In a particular aspect, the salts of the invention are provided for use in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In a further aspect, the present invention provides pharmaceutical compositions comprising a salt of the invention, and a pharmaceutical carrier, excipient or diluent. In a particular aspect, the pharmaceutical composition may additionally comprise further therapeutically active ingredients suitable for use in combination with the salts of the invention. In a more particular aspect, the further therapeutically active ingredient is an agent for the treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

Moreover, the salts of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons, which method comprises administering an effective amount of the pharmaceutical composition or salts of the invention as described herein.

The present invention also provides pharmaceutical compositions comprising a salt of the invention, and a suitable pharmaceutical carrier, excipient or diluent for use in medicine. In a particular aspect, the pharmaceutical composition is for use in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In additional aspects, this invention provides methods for synthesizing the salts of the invention, with representative synthetic protocols and pathways disclosed later on herein.

Other objects and advantages will become apparent to those skilled in the art from a consideration of the ensuing detailed description.

It will be appreciated that the salts of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms 'groups' and 'radicals' can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Salt(s) of the invention', and equivalent expressions, are meant to embrace salts of the compound according to Formula (I) (Compound 1) as herein described, which expression includes the pharmaceutically acceptable salts, and the solvates, e.g. hydrates, and the solvates of the pharmaceutically acceptable salts where the context so permits.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable vehicle' refers to a diluent, adjuvant, excipient or carrier with which a salt of the invention is administered.

'Solvate' refers to forms of the compound that are associated with a solvent, usually by a solvolysis reaction. This physical association includes hydrogen bonding. Conventional solvents include water, ethanol, acetic acid and the like. The salts of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a salt of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'inflammatory diseases' refers to the group of conditions including, rheumatoid arthritis, osteoarthritis, juvenile idiopathic arthritis, psoriasis, psoriatic arthritis, allergic airway disease (e.g. asthma, rhinitis), chronic obstructive pulmonary disease (COPD), inflammatory bowel diseases (e.g. Crohn's disease, Whipple, chronic ulcerative colitis, or colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, and inflammatory bowel diseases (e.g. Crohn's disease, Whipple, chronic ulcerative colitis, or colitis).

As used herein the term 'autoimmune disease(s)' refers to the group of diseases including obstructive airways disease, including conditions such as COPD, asthma (e.g. intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly the term refers to COPD, asthma, systemic lupus erythematosus, type I diabetes mellitus and inflammatory bowel disease.

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukaemia, acute and chronic lymphoblastic leukemia), multiple myeloma, psoriasis, restenosis, scleroderma or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukaemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma). In particular, the term "cancer" refers to acute lymphoblastic leukemia, acute myeloidleukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, asopharyngeal cancer, neuroblastoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor. More particularly, the cancer is selected from breast cancer, endometrial and cervical cancer, lung cancer, ovarian cancer, prostate cancer, hepatic cancer, and pancreatic cancer.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML), and acute lymphoblastic leukemia (ALL) and chronic lymphoblastic leukaemia (CLL).

As used herein the term 'allergy' refers to the group of conditions characterized by a hypersensitivity disorder of the immune system including, allergic airway disease (e.g. asthma, rhinitis), sinusitis, eczema and hives, as well as food allergies or allergies to insect venom.

As used herein the term 'asthma' as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate the cause.

As used herein the term 'transplant rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or esophagus, or graft-versus-host diseases.

As used herein the term 'diseases involving degradation and/or disruption of cartilage homeostasis' includes conditions such as osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'disease(s) associated with hypersecretion of IL6' includes conditions such as Castleman's disease, multiple myeloma, psoriasis, Kaposi's sarcoma and/or mesangial proliferative glomerulonephritis.

As used herein the term 'disease(s) associated with hypersecretion of interferons' includes conditions such as systemic and cutaneous lupus erythematosis, lupus nephritis, dermatomyositis, Sjogren's syndrome, psoriasis, rheumatoid arthritis.

When ranges are referred to herein, for example but without limitation, $C_{1-8}$ alkyl, the citation of a range should be considered a representation of each member of said range.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{15}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It will be appreciated that salts of the invention may be metabolized to yield biologically active metabolites.

The Invention

The present invention relates to salts of the compound cyclopropanecarboxylic acid {5-[4-(1,1-dioxo-thiomorpholin-4-ylmethyl)-phenyl]-[1,2,4]triazolo[1,5-a]pyridin-2-yl}-amide (Compound 1), and methods for the preparation of such salts, which are useful in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons. In particular, the salts of the invention inhibit JAK, a family of tyrosine kinases, and more particularly JAK1.

The present invention also provides methods for the prophylaxis and/or treatment of diseases including inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons by administering a salt of the invention, or a pharmaceutical composition containing said salt.

Accordingly, in one aspect the present invention provides a salt of a compound according to Formula (I) (Compound 1) below:

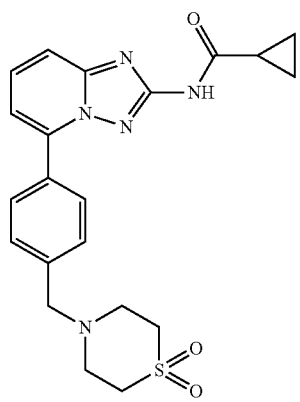

I wherein said salt is formed with a salt forming agent selected from hydrobromic acid, hydrochloric acid, sulfuric acid, toluenesulfonic acid, benzenesulfonic acid, oxalic acid, maleic acid, naphthalene-2-sulfonic acid, naphthalene-1,5-disulfonic acid, 1-2-ethane disulfonic acid, methanesulfonic acid, 2-hydroxy ethanesulfonic acid, phosphoric acid, ethane sulfonic acid, malonic acid, 2-5-dihydroxybenzoic acid, and L-Tartaric acid.

In one embodiment, the salt of the invention is one formed with a salt forming agent selected from hydrobromic acid, and hydrochloric acid, in particular hydrochloric acid.

In one embodiment, the salt of the invention is one formed with a salt forming agent selected from oxalic acid, maleic acid, or malonic acid, in particular maleic acid.

In one embodiment, the salt of the invention is one formed with a salt forming agent selected from toluenesulfonic acid, benzenesulfonic acid, naphthalene-2-sulfonic acid, and ethanesulfonic acid; in particular toluenesulfonic acid, and benzenesulfonic acid, more particularly toluenesulfonic acid, and most particularly para-toluenesulfonic acid.

In one embodiment, the salt of the invention is a 3:1 to 1:3 [Compound 1:salt forming agent] adduct. In a particular embodiment, the salt of the invention is a 1:1 [Compound 1:salt forming agent] adduct. In a more particular embodiment, the salt forming agent is selected from hydrobromic acid, hydrochloric acid, toluenesulfonic acid, and maleic acid. In a most particular embodiment, the salt forming agent is hydrochloric acid.

In one embodiment, the salt of the invention is a solvate. In a particular embodiment, the salt of the invention is a mono-, di-, or trisolvate. In a most particular embodiment, the salt of the invention is a trisolvate. Alternatively, the salt of the invention is not a solvate.

In one embodiment, the salt of the invention is a hydrate. In a more particular embodiment, the salt of the invention is a mono-, di-, or trihydrate. In a most particular embodiment, the salt of the invention is a trihydrate. Alternatively, the salt of the invention is anhydrous.

In one embodiment, the salt of the invention is a [Compound 1:Salt forming agent:Solvent] adduct. In a particular embodiment, the salt of the invention is a 1:1:0 to 1:1:4 [Compound 1:Salt forming agent:Solvent] adduct. In a more particular embodiment, the salt of the invention is a 1:1:0, 1:1:1, 1:1:1.5, 1:1:2, or 1:1:3 [Compound 1:Salt forming agent:Solvent] adduct. In a most particular embodiment, the salt of the invention is a 1:1:3 [Compound 1:Salt forming agent:Solvent] adduct.

In another embodiment, the salt of the invention is a [Compound 1:HCl:Solvent] adduct. In a particular embodiment, the salt of the invention is a 1:1:0 to 1:1:4 [Compound 1:HCl:Solvent] adduct. In a more particular embodiment, the salt of the invention is a 1:1:0, 1:1:1, 1:1:1.5, 1:1:2, or 1:1:3 [Compound 1:HCl:Solvent] adduct. In a most particular embodiment, the salt of the invention is a 1:1:3 [Compound 1:HCl:Solvent] adduct. In a further most particular embodiment, the solvent is selected from $H_2O$, MeOH, and $HCO_2H$.

In another embodiment, the salt of the invention is a [Compound 1:HCl:$H_2O$] adduct. In a particular embodiment, the salt of the invention is a 1:1:0 to 1:1:4 [Compound 1:HCl:$H_2O$] adduct. In a more particular embodiment, the salt of the invention is a 1:1:0, 1:1:1, 1:1:1.5, 1:1:2, or 1:1:3 [Compound 1:HCl:$H_2O$] adduct. In a most particular embodiment, the salt of the invention is a 1:1:3 [Compound 1:HCl:$H_2O$] adduct.

In one embodiment, the salt of the invention exhibits peaks on a XRPD spectrum.

In one embodiment, the salt of the invention is in a crystalline form.

In one embodiment, the salt of the invention is a 1:1:0 [Compound 1:HCl:$H_2O$] adduct in a solid crystalline form, wherein the crystalline form is characterized at least by a powder X-ray diffraction peak at any one or more of the following positions: 7.4, 8.9, 12.4, 14.8, 15.1, 16.9, 17.6, 19.4, 20.7, 21.1, 22.8, 24.9, 26.0, 28.6, 29.8, and 32.6° 2θ±0.2° 2θ.

In one embodiment, the salt of the invention is a 1:1:0 [Compound 1:HCl:$H_2O$] adduct in a solid crystalline form, wherein the crystalline form is characterized at least by a powder X-ray diffraction peak at least at 5, 10, 15, or more of the following positions: 7.4, 8.9, 12.4, 14.8, 15.1, 16.9, 17.6, 19.4, 20.7, 21.1, 22.8, 24.9, 26.0, 28.6, 29.8, and 32.6° 2θ±0.2° 2θ.

In one embodiment, the salt of the invention is a 1:1:0 [Compound 1:HCl:$H_2O$] adduct in a solid crystalline form, wherein the crystalline form is characterized by a powder X-ray diffraction peak in all of the following positions: 7.4, 8.9, 12.4, 14.8, 15.1, 16.9, 17.6, 19.4, 20.7, 21.1, 22.8, 24.9, 26.0, 28.6, 29.8, and 32.6° 2θ±0.2° 2θ. In a particular embodiment, the salt of the invention is characterized by the XRPD pattern expressed in terms of 2 theta angles as shown on Error! Reference source not found.

In one embodiment, the salt of the invention is a 1:1:3 [Compound 1:HCl:$H_2O$] adduct in a solid crystalline form, wherein the crystalline form is characterized at least by a powder X-ray diffraction peak at any one or more of the following positions: 7.3, 8.4, 8.8, 10.7, 12.0, 12.2, 13.2, 13.7, 14.5, 16.3, 16.7, 17.6, 19.3, 20.2, 20.6, 21.0, 21.4, 21.8, 22.8, 23.4, 23.9, 24.5, 25.2, 25.7, 25.9, 26.4, 27.2, 27.7, 28.3, 28.6, 28.9, 29.2, 29.6, and 32.7° 2θ±0.2° 2θ.

In a particular embodiment, the salt of the invention is a 1:1:3 [Compound 1:HCl:$H_2O$] adduct in a solid crystalline form, wherein the crystalline form is characterized at least by a powder X-ray diffraction peak at least at 5, 10, 15, 20, 25, 30 or more of the following positions: 7.3, 8.4, 8.8, 10.7, 12.0, 12.2, 13.2, 13.7, 14.5, 16.3, 16.7, 17.6, 19.3, 20.2, 20.6, 21.0, 21.4, 21.8, 22.8, 23.4, 23.9, 24.5, 25.2, 25.7, 25.9, 26.4, 27.2, 27.7, 28.3, 28.6, 28.9, 29.2, 29.6, and 32.7° 2θ±0.2° 2θ.

In one embodiment, the salt of the invention is a 1:1:3 [Compound 1:HCl:$H_2O$] adduct in a solid crystalline form, wherein the crystalline form is characterized by a powder X-ray diffraction peak in all of the following positions: 7.3, 8.4, 8.8, 10.7, 12.0, 12.2, 13.2, 13.7, 14.5, 16.3, 16.7, 17.6, 19.3, 20.2, 20.6, 21.0, 21.4, 21.8, 22.8, 23.4, 23.9, 24.5, 25.2, 25.7, 25.9, 26.4, 27.2, 27.7, 28.3, 28.6, 28.9, 29.2, 29.6, and 32.7° 2θ±0.2° 2θ. In a particular embodiment, the salt of the invention is characterized by the XRPD pattern expressed in terms of 2 theta angles as shown on Error! Reference source not found.

In one embodiment, the 1:1:3 [Compound 1:HCl:$H_2O$] adduct in a solid crystalline form has a particle size of less than 1000 μM, as measured by laser diffraction (Table II). In a particular embodiment, the 1:1:3 [Compound 1:HCl:$H_2O$] adduct in a solid crystalline form has a particle size between 50 μm and 800 μm. In a more particular embodiment, the 1:1:3 [Compound 1:HCl:$H_2O$] adduct in a solid crystalline form has a particle size between 200 μm and 600 μm.

In one embodiment, the salt of the invention is a 1:1:1 [Compound 1:HCl:MeOH] adduct in a solid crystalline form, wherein the crystalline form is characterized at least by a powder X-ray diffraction peak at any one or more of the following positions: 7.1, 14.4, 16.6, 17.3, 18.9, 23.4, 24.8, and 29.0° 2θ±0.2° 2θ.

In a particular embodiment, the salt of the invention is a 1:1:1 [Compound 1:HCl:MeOH] adduct in a solid crystalline form, wherein the crystalline form is characterized at least by a powder X-ray diffraction peak at least at 3, 5, 7 or more of the following positions: 7.1, 14.4, 16.6, 17.3, 18.9, 23.4, 24.8, and 29.0° 2θ±0.2° 2θ.

In one embodiment, the salt of the invention is a 1:1:1 [Compound 1:HCl:MeOH] adduct in a solid crystalline form, wherein the crystalline form is characterized by a powder X-ray diffraction peak in all of the following positions: 7.1, 14.4, 16.6, 17.3, 18.9, 23.4, 24.8, and 29.0° 2θ±0.2° 2θ. In a particular embodiment, the salt of the invention is characterized by the XRPD pattern expressed in terms of 2 theta angles as shown on Error! Reference source not found.

In one embodiment, the salt of the invention is a 1:1:1.5 [Compound 1:HCl:HCO$_2$H] adduct in a solid crystalline form, wherein the crystalline form is characterized at least by a powder X-ray diffraction peak at any one or more of the following positions: 7.1, 14.4, 14.8, 16.4, 17.4, 18.6, 20.8, 23.4, 24.5, 24.9, and 29.0° 2θ±0.2° 2θ.

In one embodiment, the salt of the invention is a 1:1:1.5 [Compound 1:HCl:HCO$_2$H] adduct in a solid crystalline form, wherein the crystalline form is characterized at least by a powder X-ray diffraction peak at least at 3, 5, 7, 9 or more of the following positions: 7.1, 14.4, 14.8, 16.4, 17.4, 18.6, 20.8, 23.4, 24.5, 24.9, and 29.0° 2θ±0.2° 2θ.

In one embodiment, the salt of the invention is a 1:1:1.5 [Compound 1:HCl:HCO$_2$H] adduct in a solid crystalline form, wherein the crystalline form is characterized by a powder X-ray diffraction peak in all of the following positions: 7.1, 14.4, 14.8, 16.4, 17.4, 18.6, 20.8, 23.4, 24.5, 24.9, and 29.0° 2θ±0.2° 2θ. In a particular embodiment, the salt of the invention is characterized by the XRPD pattern expressed in terms of 2 theta angles as shown on Error! Reference source not found.

In one embodiment, a salt of the invention is obtained by combining a Compound 1, with an acid selected from hydrobromic acid, hydrochloric acid, sulfuric acid, toluenesulfonic acid, benzenesulfonic acid, oxalic acid, maleic acid, naphthalene-2-sulfonic acid, naphthalene-1,5-disulfonic acid, 1-2-ethane disulfonic acid, methanesulfonic acid, 2-hydroxy ethanesulfonic acid, phosphoric acid, ethane sulfonic acid, malonic acid, 2-5-dihydroxybenzoic acid, and L-Tartaric acid, in an inert solvent and precipitating said salt from said solvent. In a particular embodiment, the salt of the invention is obtained by adding Compound 1 and a salt forming agent in a suitable solvent in order to achieve full dissolution, followed by a controlled solvent evaporation in order to achieve supersaturation, and thus crystallization of the corresponding salt.

In one embodiment, the salt of the invention is obtained by mixing Compound 1, and an acid in a molar ratio of between 5:1 and 1:5 of Compound 1:acid. In a particular embodiment, the salt of the invention is obtained by mixing Compound 1, and an acid in a molar ratio of between 2:1 and 1:2 of Compound 1:acid. In a more particular embodiment, the salt of the invention is obtained by mixing a Compound 1 and an acid in a molar ratio of 1:1.

In another particular embodiment, the solvent for the preparation of the salt of the invention is selected from ketones, alcohols, esters, C$_{1-10}$ alkyl, C$_{3-7}$ cycloalkyl, C$_{6-10}$ monocyclic or fused bicyclic aryl, sulfoxide, C$_{1-10}$ alkylnitrile, C$_{1-10}$ linear, branched or cyclic ethers, and C$_{1-10}$ haloalkyl, In a particular embodiment, the solvent for the preparation of the salt of the invention is selected from acetone, anisole, butanol, butyl acetate, TBME, DMSO, ethanol, ethyl acetate, heptane, isopropyl acetate, MEK, isopropyl acetate, MeCN, cyclohexane, DCM, dioxane, methanol, nitromethane, THF, methyl THF, toluene, water, 10% aqueous acetone, 10% aqueous THF, and 10% methanol. In a particular embodiment, the solvent for the preparation of the salt of the invention is selected from dioxane, THF, acetone, DCM, and MeOH.

In another aspect is provided a method for preparing the salt of the invention comprising the steps of
i) reacting Compound 1, with an acid selected from hydrobromic acid, hydrochloric acid, sulfuric acid, toluenesulfonic acid, benzenesulfonic acid, oxalic acid, maleic acid, naphthalene-2-sulfonic acid, naphthalene-1,5-disulfonic acid, 1-2-ethane disulfonic acid, methanesulfonic acid, 2-hydroxy ethanesulfonic acid, phosphoric acid, ethane sulfonic acid, malonic acid, 2-5-dihydroxybenzoic acid, and L-Tartaric acid, in an inert solvent; and
ii) precipitating the said salt from the said solvent.

In a further aspect, is provided a salt of the invention obtainable by or obtained by the aforementioned method.

In one embodiment, with respect to the preparation of the salt of the invention, the inert solvent is selected from dioxane, THF, acetone, DCM, and MeOH.

In one embodiment, with respect to the preparation of the salt of the invention, the inert solvent is DCM.

In one embodiment, with respect to the preparation of the salt of the invention, the inert solvent is selected from iPrOH/water, iPrOH, iBuOH, and tBuOH.

In one embodiment is provided a method for preparing a [Compound 1:HCl:3H$_2$O] adduct in a solid crystalline form comprising the steps of:
i) Stirring the Compound 1 with water,
ii) Adding aqueous HCl,
iii) Stirring further the mixture obtained at step ii),
iv) Cooling the mixture of step iii) to 15° C.,
v) Continuing stirring for at most 24 h at 15° C.,
vi) separating the resulting solid by filtration obtained in the previous step v), and
vii) drying under nitrogen for at least 4 h said resulting solid obtained in the previous step vi).

In a particular embodiment is provided a method for preparing a [Compound 1:HCl:3H$_2$O] adduct in a solid crystalline form comprising the steps of:
i) Stirring the Compound 1 with water at 50° C.,
ii) Adding aqueous HCl,
iii) Stirring the mixture obtained at step ii) further at 50° C. for 15 min,
iv) Cooling the mixture of step iii) to 15° C.,
v) Continuing stirring for 12 h to 24 h at 15° C.,
vi) separating the resulting solid by filtration obtained in the previous step v), and
vii) drying under nitrogen for at least 4 h said resulting solid obtained in the previous step vi).

In another embodiment is provided a method for preparing a [Compound 1:HCl:3H$_2$O] adduct in a solid crystalline form comprising the steps of:
i) mixing Compound 1 suspended in DCM, with MeOH,
ii) adding water under stirring,
iii) separating the organic layer,
iv) adding a solution of HCl to the organic layer obtained in the previous step iii),
v) separating the resulting solid by filtration obtained in the previous step iv),
vi) drying said resulting solid obtained in the previous step v),
vii) adding the solid obtained in the previous step vi) to a formic acid/water solution, under stirring,
viii) adding water to the solution obtained in the previous step vii),
ix) separating by filtration the resulting solid obtained in the previous step viii), and
x) drying the resulting solid obtained in the previous step ix).

In another embodiment is provided a method for preparing a [Compound 1:HCl:3H$_2$O] adduct in a solid crystalline form comprising the steps of:
i) mixing Compound 1 suspended in DCM, with MeOH at 35° C.,
ii) adding water under stirring at 35° C. for at least 15 min,
iii) separating the organic layer, iv) adding a 10% w/w solution of HCl in MeOH to the organic layer obtained in the previous step iii),
v) separating the resulting solid by filtration obtained in the previous step iv),
vi) drying said resulting solid obtained in the previous step v),
vii) adding the solid obtained in the previous step vi) to a 1.6/0.4 formic acid/water solution, under stirring at 55° C.
viii) adding water to the solution obtained in the previous step vii),
ix) separating by filtration the resulting solid obtained in the previous step viii), and
x) drying the resulting solid obtained in the previous step ix).

In another embodiment is provided a method for preparing a [Compound 1:HCl:3H$_2$O] adduct in a solid crystalline form comprising the steps of:
i) reacting Compound 1 suspended in DCM, with MeOH and trimercaptotriazine trisodium,
ii) filtering the resulting suspension,
iii) adding water under stirring,
iv) separating the organic layer,
v) adding a solution of HCl to the organic layer obtained at step iv),
vi) separating the resulting solid by filtration obtained at step v),
vii) drying said resulting solid obtained at step vi),
viii) adding the solid obtained at step vii) to a formic acid/water solution, under stirring,
ix) adding water to the solution of step viii),
x) separating by filtration the resulting solid obtained at step ix), and
xi) drying the resulting solid obtained at step x).

In another aspect is provided a method for preparing a [Compound 1:HCl:3H$_2$O] adduct in a solid crystalline form comprising the steps of:
i) reacting Compound 1 suspended in DCM, with MeOH and trimercaptotriazine trisodium at 35° C. for at least 5 h,
ii) filtering the resulting suspension,
iii) adding water under stirring at 35° C. for at least 15 min,
iv) separating the organic layer,
v) adding a 10% w/w solution of HCl in MeOH to the organic layer obtained at step iv),
vi) separating the resulting solid by filtration obtained at step v),
vii) drying said resulting solid obtained at step vi),
viii) adding the solid obtained at step vii) to a 1.6/0.4 formic acid/water solution, under stirring at 55° C.,
ix) adding water to the solution of step viii),
x) separating by filtration the resulting solid obtained at step ix), and
xi) drying the resulting solid obtained at step x).

Alternatively, the exclusion of one or more of the specified variables from a group or an embodiment, or combinations thereof is also contemplated by the present invention.

Pharmaceutical Compositions

When employed as a pharmaceutical, a salt of the invention is typically administered in the form of a pharmaceutical composition. Such compositions can be prepared in a manner well known in the pharmaceutical art and comprise at least one active salt of the invention.

Generally, a salt of the invention is administered in a pharmaceutically effective amount. The amount of salt of the invention actually administered will typically be determined by a physician, in the light of the relevant circumstances, including the condition to be treated, the chosen route of administration, the actual salt of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a salt of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the salt of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavours and the like. Solid forms may include, for example, any of the following ingredients, or salt of the inventions of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavouring agent such as peppermint or orange flavouring.

Injectable compositions are typically based upon injectable sterile saline or phosphate-buffered saline or other injectable carriers known in the art. As before, the active salt of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A salt of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

A salt of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1

Tablets

A salt of the invention may be admixed as a dry powder with a dry gelatin binder in an approximate 1:2 weight ratio. A minor amount of magnesium stearate may be added as a lubricant. The mixture may be formed into 240-270 mg tablets (80-90 mg of active salt of the invention per tablet) in a tablet press.

Formulation 2

Capsules

A salt of the invention may be admixed as a dry powder with a starch diluent in an approximate 1:1 weight ratio. The mixture may be filled into 250 mg capsules (125 mg of active salt of the invention per capsule).

Formulation 3

Liquid

A salt of the invention (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavour, and colour may be diluted with water and added with stirring. Sufficient water may then be added with stirring. Further sufficient water may be then added to produce a total volume of 5 mL.

Formulation 4

Tablets

A salt of the invention may be admixed as a dry powder with a dry gelatin binder in an approximate 1:2 weight ratio. A minor amount of lubritab may be added as a lubricant. The mixture may be formed into 25-900 mg tablets (8-300 mg of active salt of the invention) in a tablet press.

Formulation 5

Injection

A salt of the invention may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of A salt of the invention (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides salts of the invention, or pharmaceutical compositions comprising a salt of the invention, for use in medicine. In a particular embodiment, the present invention provides salts of the invention or pharmaceutical compositions comprising a salt of the invention, for use in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In one embodiment, the present invention provides the use of a salt of the invention, or pharmaceutical compositions comprising a salt of the invention in medicine. In a particular embodiment, the present invention provides salts of the invention or pharmaceutical compositions comprising a salt of the invention, for use in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In another embodiment, the present invention provides salts of the invention, or pharmaceutical compositions comprising a salt of the invention for use in the manufacture of a medicament for use in the prophylaxis and/or treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In additional method of treatment aspects, this invention provides methods of prophylaxis and/or treatment of a mammal afflicted with inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons, which methods comprise the administration of an effective amount of a salt of the invention or one or more of the pharmaceutical compositions herein described for the treatment or prophylaxis of said condition.

In one embodiment, the present invention provides pharmaceutical compositions comprising a salt of the invention, and another therapeutic agent. In a particular embodiment, the other therapeutic agent is an agent for the treatment of inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons.

In one embodiment, the present invention provides salts of the invention or pharmaceutical compositions comprising a salt of the invention, for use in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease, Whipple, chronic ulcerative colitis, or colitis). More particularly, the inflammatory disease is selected from rheumatoid arthritis, and inflammatory bowel diseases (e.g. Crohn's disease, Whipple, chronic ulcerative colitis, or colitis).

In one embodiment, the present invention provides the use of a salt of the invention or pharmaceutical compositions comprising a salt of the invention, in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease, Whipple, chronic ulcerative colitis, or colitis). More particularly, the inflammatory disease is selected from rheumatoid arthritis, and inflammatory bowel diseases (e.g. Crohn's disease, Whipple, chronic ulcerative colitis, or colitis).

In another embodiment, the present invention provides salts of the invention, or pharmaceutical compositions comprising a salt of the invention for use in the manufacture of a medicament for use in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease, Whipple, chronic ulcerative colitis, or colitis). More particularly, the inflammatory disease is selected from rheumatoid arthritis, and inflammatory bowel diseases (e.g. Crohn's disease, Whipple, chronic ulcerative colitis, or colitis).

In additional method of treatment aspects, this invention provides methods of prophylaxis and/or treatment of a mammal afflicted with inflammatory diseases, which methods comprise the administration of an effective amount of a salt of the invention or one or more of the pharmaceutical compositions herein described for the treatment or prophylaxis of said condition. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease, Whipple, chronic ulcerative colitis, or colitis). More particularly, the inflammatory disease is selected from rheumatoid arthritis, and inflammatory bowel diseases (e.g. Crohn's disease, Whipple, chronic ulcerative colitis, or colitis).

In one embodiment, the present invention provides salts of the invention or pharmaceutical compositions comprising a salt of the invention, for use in the prophylaxis and/or treatment of autoimmune diseases. In a particular embodiment, the autoimmune disease is selected from COPD, asthma (e.g. intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly, the autoimmune disease is selected from COPD, asthma, systemic lupus erythematosus, type I diabetes mellitus and inflammatory bowel disease.

In one embodiment, the present invention provides the use of a salt of the invention or pharmaceutical compositions comprising a salt of the invention, in the prophylaxis and/or treatment of autoimmune diseases. In a particular embodiment, the autoimmune disease is selected from COPD, asthma (e.g. intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly, the autoimmune disease is selected from COPD, asthma, systemic lupus erythematosus, type I diabetes mellitus and inflammatory bowel disease.

In another embodiment, the present invention provides salts of the invention, or pharmaceutical compositions comprising a salt of the invention for use in the manufacture of a medicament for use in the prophylaxis and/or treatment of autoimmune diseases. In a particular embodiment, the autoimmune disease is selected from COPD, asthma (e.g. intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly, the autoimmune disease is selected from COPD, asthma, systemic lupus erythematosus, type I diabetes mellitus and inflammatory bowel disease.

In additional method of treatment aspects, this invention provides methods of prophylaxis and/or treatment of a mammal afflicted with autoimmune diseases, which methods comprise the administration of an effective amount of a salt of the invention or one or more of the pharmaceutical compositions herein described for the treatment or prophylaxis of said condition. In a particular embodiment, the autoimmune disease is selected from COPD, asthma (e.g. intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythematosus, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease, Whipple, chronic ulcerative colitis, or colitis), atherosclerosis and amyotrophic lateral sclerosis. Particularly, the autoimmune disease is selected from COPD, asthma, systemic lupus erythematosus, type I diabetes mellitus and inflammatory bowel disease.

In one embodiment, the present invention provides salts of the invention or pharmaceutical compositions comprising a salt of the invention, for use in the prophylaxis and/or treatment of proliferative diseases. In a particular embodiment, the proliferative disease is selected from cancer, and leukaemia. In a more particular embodiment, the proliferative disease is selected from breast cancer, endometrial and cervical cancer, lung cancer, ovarian cancer, prostate cancer, hepatic cancer, and pancreatic cancer.

In one embodiment, the present invention provides the use of a salt of the invention or pharmaceutical compositions comprising a salt of the invention, in the prophylaxis and/or treatment of proliferative diseases. In a particular embodiment, the proliferative disease is selected from cancer, and leukaemia. In a more particular embodiment, the proliferative disease is selected from breast cancer, endometrial and cervical cancer, lung cancer, ovarian cancer, prostate cancer, hepatic cancer, and pancreatic cancer.

In another embodiment, the present invention provides salts of the invention, or pharmaceutical compositions comprising a salt of the invention for use in the manufacture of a medicament for use in the prophylaxis and/or treatment of proliferative diseases. In a particular embodiment, the proliferative disease is selected from cancer, and leukaemia. In a more particular embodiment, the proliferative disease is selected from breast cancer, endometrial and cervical cancer, lung cancer, ovarian cancer, prostate cancer, hepatic cancer, and pancreatic cancer.

In additional method of treatment aspects, this invention provides methods of prophylaxis and/or treatment of a mammal afflicted with proliferative diseases, which methods comprise the administration of an effective amount of a salt of the invention or one or more of the pharmaceutical compositions herein described for the treatment or prophylaxis of said condition. In a particular embodiment, the proliferative disease is selected from cancer, and leukaemia. In a more particular embodiment, the proliferative disease is selected from breast cancer, endometrial and cervical cancer, lung cancer, ovarian cancer, prostate cancer, hepatic cancer, and pancreatic cancer.

In one embodiment, the present invention provides salts of the invention or pharmaceutical compositions comprising a salt of the invention, for use in the prophylaxis and/or treatment of allergy. In a particular embodiment, the allergy is selected from allergic airway disease (e.g. asthma, rhinitis), sinusitis, eczema and hives, as well as food allergies or allergies to insect venom.

In one embodiment, the present invention provides the use of a salt of the invention or pharmaceutical compositions comprising a salt of the invention, in the prophylaxis and/or treatment of allergy. In a particular embodiment, the allergy is selected from allergic airway disease (e.g. asthma, rhinitis), sinusitis, eczema and hives, as well as food allergies or allergies to insect venom.

In another embodiment, the present invention provides salts of the invention, or pharmaceutical compositions comprising a salt of the invention for use in the manufacture of a medicament for use in the prophylaxis and/or treatment of allergy. In a particular embodiment, the allergy is selected from allergic airway disease (e.g. asthma, rhinitis), sinusitis, eczema and hives, as well as food allergies or allergies to insect venom.

In additional method of treatment aspects, this invention provides methods of prophylaxis and/or treatment of a mammal afflicted with allergy, which methods comprise the administration of an effective amount of a salt of the invention or one or more of the pharmaceutical compositions herein described for the treatment or prophylaxis of said condition. In a particular embodiment, the allergy is selected from allergic airway disease (e.g. asthma, rhinitis), sinusitis, eczema and hives, as well as food allergies or allergies to insect venom.

In one embodiment, the present invention provides salts of the invention or pharmaceutical compositions comprising a salt of the invention, for use in the prophylaxis and/or treatment of transplant rejection.

In one embodiment, the present invention provides the use of a salt of the invention or pharmaceutical compositions comprising a salt of the invention, in the prophylaxis and/or treatment of transplant rejection.

In another embodiment, the present invention provides salts of the invention, or pharmaceutical compositions comprising a salt of the invention for use in the manufacture of a medicament for use in the prophylaxis and/or treatment of transplant rejection.

In additional method of treatment aspects, this invention provides methods of prophylaxis and/or treatment of a mammal afflicted with transplant rejection, which methods comprise the administration of an effective amount of a salt of the invention or one or more of the pharmaceutical compositions herein described for the treatment or prophylaxis of said condition.

In one embodiment, the present invention provides salts of the invention or pharmaceutical compositions comprising a salt of the invention, for use in the prophylaxis and/or treatment of diseases involving degradation and/or disruption of cartilage homeostasis. In a particular embodiment, the diseases involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

In one embodiment, the present invention provides the use of a salt of the invention or pharmaceutical compositions comprising a salt of the invention, in the prophylaxis and/or treatment of diseases involving degradation and/or disruption of cartilage homeostasis. In a particular embodiment, the diseases involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

In another embodiment, the present invention provides salts of the invention, or pharmaceutical compositions comprising a salt of the invention for use in the manufacture of a medicament for use in the prophylaxis and/or treatment of diseases involving degradation and/or disruption of cartilage homeostasis. In a particular embodiment, the diseases involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

In additional method of treatment aspects, this invention provides methods of prophylaxis and/or treatment of a mammal afflicted with diseases involving degradation and/or disruption of cartilage homeostasis, which methods comprise the administration of an effective amount of a salt of the invention or one or more of the pharmaceutical compositions herein described for the treatment or prophylaxis of said condition. In a particular embodiment, the diseases involving degradation and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis.

In one embodiment, the present invention provides salts of the invention or pharmaceutical compositions comprising a salt of the invention, for use in the prophylaxis and/or treatment of congenital cartilage malformation(s). In a particular embodiment, the congenital cartilage malformation(s) is selected from hereditary chondrolysis, chondrodysplasias and pseudochondrodysplasias, in particular, but without limitation, microtia, anotia, metaphyseal chondrodysplasia, and related disorders.

In one embodiment, the present invention provides the use of a salt of the invention or pharmaceutical compositions comprising a salt of the invention, in the prophylaxis and/or treatment of congenital cartilage malformation(s). In a particular embodiment, the congenital cartilage malformation(s) is selected from hereditary chondrolysis, chondrodysplasias and pseudochondrodysplasias, in particular, but without limitation, microtia, anotia, metaphyseal chondrodysplasia, and related disorders.

In another embodiment, the present invention provides salts of the invention, or pharmaceutical compositions comprising a salt of the invention for use in the manufacture of a medicament for use in the prophylaxis and/or treatment of congenital cartilage malformation(s). In a particular embodiment, the congenital cartilage malformation(s) is selected from hereditary chondrolysis, chondrodysplasias and pseudochondrodysplasias, in particular, but without limitation, microtia, anotia, metaphyseal chondrodysplasia, and related disorders.

In additional method of treatment aspects, this invention provides methods of prophylaxis and/or treatment of a mammal afflicted with congenital cartilage malformation(s), which methods comprise the administration of an effective amount of a salt of the invention or one or more of the pharmaceutical compositions herein described for the treatment or prophylaxis of said condition. In a particular embodiment, the congenital cartilage malformation(s) is selected from hereditary chondrolysis, chondrodysplasias and pseudochondrodysplasias, in particular, but without limitation, microtia, anotia, metaphyseal chondrodysplasia, and related disorders.

In one embodiment, the present invention provides salts of the invention or pharmaceutical compositions comprising a salt of the invention, for use in the prophylaxis and/or treatment of disease(s) associated with hypersecretion of IL6. In a particular embodiment, the disease(s) associated with hypersecretion of IL6 is selected from Castleman's disease, multiple myeloma, psoriasis, Kaposi's sarcoma and/or mesangial proliferative glomerulonephritis.

In one embodiment, the present invention provides the use of a salt of the invention or pharmaceutical compositions comprising a salt of the invention, in the prophylaxis and/or treatment of disease(s) associated with hypersecretion of IL6. In a particular embodiment, the disease(s) associated with hypersecretion of IL6 is selected from Castleman's disease, multiple myeloma, psoriasis, Kaposi's sarcoma and/or mesangial proliferative glomerulonephritis.

In another embodiment, the present invention provides salts of the invention, or pharmaceutical compositions comprising a salt of the invention for use in the manufacture of a medicament for use in the prophylaxis and/or treatment of disease(s) associated with hypersecretion of IL6. In a particular embodiment, the disease(s) associated with hypersecretion of IL6 is selected from Castleman's disease, multiple myeloma, psoriasis, Kaposi's sarcoma and/or mesangial proliferative glomerulonephritis.

In additional method of treatment aspects, this invention provides methods of prophylaxis and/or treatment of a mammal afflicted with disease(s) associated with hypersecretion of IL6, which methods comprise the administration of an effective amount of a salt of the invention or one or more of the pharmaceutical compositions herein described for the treatment or prophylaxis of said condition. In a particular embodiment, the disease(s) associated with hypersecretion of IL6 is selected from Castleman's disease, multiple myeloma, psoriasis, Kaposi's sarcoma and/or mesangial proliferative glomerulonephritis.

In one embodiment, the present invention provides salts of the invention or pharmaceutical compositions comprising a salt of the invention, for use in the prophylaxis and/or treatment of disease(s) associated with hypersecretion of interferons. In a particular embodiment, the disease associated with hypersecretion of interferons is selected from systemic and cutaneous lupus erythematosus, lupus nephritis, dermatomyositis, Sjogren's syndrome, psoriasis, and rheumatoid arthritis.

In one embodiment, the present invention provides the use of a salt of the invention or pharmaceutical compositions comprising a salt of the invention, in the prophylaxis and/or treatment of disease(s) associated with hypersecretion of interferons. In a particular embodiment, the disease associated with hypersecretion of interferons is selected from systemic and cutaneous lupus erythematosus, lupus nephritis, dermatomyositis, Sjogren's syndrome, psoriasis, and rheumatoid arthritis.

In another embodiment, the present invention provides salts of the invention, or pharmaceutical compositions comprising a salt of the invention for use in the manufacture of a medicament for use in the prophylaxis and/or treatment of disease(s) associated with hypersecretion of interferons. In a particular embodiment, the disease associated with hypersecretion of interferons is selected from systemic and cutaneous lupus erythematosus, lupus nephritis, dermatomyositis, Sjogren's syndrome, psoriasis, and rheumatoid arthritis.

In additional method of treatment aspects, this invention provides methods of prophylaxis and/or treatment of a mammal afflicted with disease(s) associated with hypersecretion of interferons, which methods comprise the administration of an effective amount of a salt of the invention or one or more of the pharmaceutical compositions herein described for the treatment or prophylaxis of said condition. In a particular embodiment, the disease associated with hypersecretion of interferons is selected from systemic and cutaneous lupus erythematosus, lupus nephritis, dermatomyositis, Sjogren's syndrome, psoriasis, and rheumatoid arthritis.

A particular regimen of the present method comprises the administration to a subject suffering from inflammatory conditions, autoimmune diseases, proliferative diseases, allergy, transplant rejection, diseases involving degradation and/or disruption of cartilage homeostasis, congenital cartilage malformations, and/or diseases associated with hypersecretion of IL6 or interferons, of an effective amount of a salt of the invention for a period of time sufficient to reduce the level of the aforementioned diseases in the subject, and preferably terminate the processes responsible for said diseases.

Using these dosing patterns, each dose provides from about 1 to about 500 mg of the salt of the invention, with particular doses each providing from about 10 to about 300 mg, more particularly about 25 to about 250 mg, and especially 10 mg, 20 mg, 25 mg, 50 mg, 75 mg, 100 mg, 150 mg, 200 mg, 250 mg, or 300 mg.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 500 mg of the salt of the invention, with particular doses each providing from about 10 to about 300 mg, more particularly about 25 to about 250 mg, and especially 10 mg, 20 mg, 25 mg, 50 mg, 75 mg, 100 mg, 150 mg, 200 mg, 250 mg, or 300 mg.

Transdermal doses are generally selected to provide similar or lower blood levels than are achieved using injection doses.

When used to prevent the onset of a condition, a salt of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A salt of the invention can be administered as the sole active agent or it can be administered in combination with other therapeutic agents, including other salt of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a salt of the invention or a pharmaceutical composition comprising a salt of the invention is administered as a medicament. In a specific embodiment, said pharmaceutical composition additionally comprises a further active ingredient.

In one embodiment, a salt of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a salt of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a salt of the invention is co-administered with another therapeutic agent for the treatment and/or prophylaxis of proliferative disorders, particular agents include but are not limited to: methotrexate, leukovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™) capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® and hsp90 inhibitors (e.g. 17-AAG). Additionally, the salt of the invention according to Formula I may be administered in combination with other therapies including, but not limited to, radiotherapy or surgery. In a specific embodiment the proliferative disorder is selected from cancer, myeloproliferative disease or leukaemia.

In one embodiment, a salt of the invention is co-administered with another therapeutic agent for the treatment and/or prophylaxis of autoimmune diseases, particular agents include but are not limited to: glucocorticoids, cytostatic agents (e.g. purine analogs), alkylating agents, (e.g. nitrogen mustards (cyclophosphamide), nitrosoureas, platinum salt of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, fingolimod and myriocin.

In one embodiment, a salt of the invention is co-administered with another therapeutic agent for the treatment and/or prophylaxis of transplant rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, a salt of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled). Long-acting β2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine) and vasoconstrictors (e.g. oxymethazoline, xylometazoline, nafazoline and tramazoline).

Additionally, a salt of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a salt of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a salt of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a salt of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™ Enbrel™, Humira™, Remicade™, Raptiva™ and ustekinumab (a IL 12 and IL-23 blocker). Additionally, a salt of the invention may be administered in combination with other therapies including, but not limited to phototherapy, or photochemotherapy (e.g. psoralen and ultraviolet A phototherapy (PUVA)).

In one embodiment, a salt of the invention is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anti-cholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compound according to Formula I, and the salts of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Greene, T W; Wuts, P G M; 1991).

The following methods are presented with details as to the preparation of a salt of the invention as defined hereinabove and the comparative examples. A salt of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica gel 60 (35-70 µm). Thin layer chromatography is carried out using pre-coated silica gel F-254 plates (thickness 0.25 mm). $^1$H NMR spectra are recorded on a Bruker DPX 400 NMR spectrometer (400 MHz or a Bruker Advance 300 NMR spectrometer (300 MHz). Chemical shifts (δ) for 1H NMR spectra are reported in parts per million (ppm) relative to tetramethylsilane (δ 0.00) or the appropriate residual solvent peak, i.e. CHCl$_3$ (δ 7.27), as internal reference. Multiplicities are given as singlet (s), doublet (d), triplet (t), quartet (q), quintuplet (quin), multiplet (m) and broad (br). Electrospray MS spectra are obtained on a Waters platform LC/MS spectrometer or with Waters Acquity H-Class UPLC coupled to a Waters Mass detector 3100 spectrometer. Columns used: Waters Acquity UPLC BEH C18 1.7 µm, 2.1 mm ID×50 mm L, Waters Acquity UPLC BEH C18 1.7 µm, 2.1 mm ID×30 mm L, or Waters Xterra MS 5 µm C18, 100×4.6 mm. The methods are using either MeCN/H$_2$O gradients (H$_2$O contains either 0.1% TFA or 0.1% NH$_3$) or MeOH/H$_2$O gradients (H$_2$O contains 0.05% TFA). Microwave heating is performed with a Biotage Initiator.

TABLE I

List of abbreviations used in the experimental section:

| Abbreviation | Definition |
|---|---|
| APMA | 4-aminophenylmercuric acetate |
| app t | Apparent triplet |
| ATP | Adenosine-5'-triphosphate |
| AUC | Area Under the Curve |
| bd | Broad doublet |
| bs | Broad singlet |
| BSA | Bovine serum albumine |
| bt | Broad triplet |
| Cat. | Catalytic amount |
| cDNA | copy deoxyribonucleic acid |
| d | doublet |
| DCM | Dichloromethane |
| Desc'd | Described in details |
| DLM | Data Logger Module |
| DMSO | Dimethylsulfoxide |
| DSC | Differential scanning calorimetry |
| DTT | Dithiothreitol |
| DVS | Dynamic vapor sorption |
| EDTA | Ethylenediaminetetraacetic acid |
| eq. | Equivalent |

TABLE I-continued

List of abbreviations used in the experimental section:

| Abbreviation | Definition |
|---|---|
| Et$_2$O | Diethyl ether |
| EtOAc | Ethyl acetate |
| EtOH | Ethanol |
| FBS | Fetal bovine serum |
| FT-IR | Fourier transformed Infra-red spectroscopy |
| g | gram |
| GVS | Gravimetric Vapour Sorption |
| h | hour |
| HPLC | High pressure liquid chromatography |
| HP-β-CD | 2-Hydroxypropyl-beta-cyclodextrin |
| HRP | horseradish peroxydase |
| IL | Interleukin |
| Int | Intermediate |
| kg | kilogram |
| L | litre |
| LC-MS | Liquid Chromatography- Mass Spectrometry |
| LPC | lysophosphatidylcholine |
| m | multiplet |
| MeCN | Acetonitrile |
| MEK | Methyl ethyl ketone |
| MeOH | Methanol |
| µL | microliter |
| mg | milligram |
| min | minute |
| mL | millilitre |
| mmol | millimoles |
| MMP | Matrix Metallo Proteinase |
| MS Ms'd | Mass measured by LC-MS |
| MW | Molecular weight |
| N.A. | Not available |
| NBS | N-Bromosuccinimide |
| nBuOH | n-Butanol |
| NMR | Nuclear Magnetic Resonance |
| ONPG | Ortho-nitrophényl-β-galactoside |
| Patt | Pattern |
| PBF | phosphate buffered formalin |
| PBS | Phosphate buffered saline |
| PCR | Polymerase chain reaction |
| Pd(PPh$_3$)$_4$ | Tetrakis(triphenylphosphine)palladium(0) |
| Pd/C | Palladium on Carbon 10% |
| Pd$_2$(dba)$_3$ | Tris(dibenzylideneacetone) dipalladium(0) |
| PdCl$_2$dppf | [1,1'- Bis(diphenylphosphino)ferrocene] dichloropalladium(II) |
| PEG | Polyethylene glycol |
| ppm | part-per-million |
| XRPD | Powder X-Ray Diffraction |
| q | quadruplet |
| QrtPCR | quantitative real-time PCR |
| QTL | quantitative trait loci |
| rel vol | Relative volumes |
| RH | Relative humidity |
| RNA | Ribonucleic acid |
| Rt | retention time |
| s | singlet |
| sept | septuplet |
| SS-NMR | Solid state Nuclear Magnetic Resonance |
| SDTA | Simultaneous differential thermal analysis |
| t | triplet |
| TBME | tButyl methyl ether |
| TEA | Triethylamine |
| TFA | Trifluoroacetic acid |
| TGA | Thermogravimetric analysis |
| THF | Tetrahydrofuran |

TABLE II

Salt study apparatus

| | |
|---|---|
| Chemical Purity Determination by UPLC | Purity analysis is performed on a Waters Acquity system equipped with a diode array detector and Micromass ZQ mass spectrometer using MassLynx software. |

TABLE II-continued

| | Salt study apparatus |
|---|---|
| TGA | TGA data are collected on a Mettler TGA/SDTA 851e equipped with a 34 position auto-sampler. The instrument is temperature calibrated using certified indium. Typically 5-30 mg of each sample is loaded onto a pre-weighed aluminium crucible and is heated at 10° C./min from ambient temperature to 400° C. A nitrogen purge at 50 mL/min is maintained over the sample. The instrument control and data analysis software is STARe v9.10. |
| Thermodynamic Aqueous Solubility by HPLC | Aqueous solubility is determined by suspending sufficient compound in water or buffer to give a maximum final concentration of ≥1 mg · mL$^{-1}$ of the parent free-form of the compound. Quantitation is made by HPLC with reference to a standard calibration curve. The solubility is calculated using the peak areas determined by integration of the peak found at the same retention time as the principal peak in the standard injection. |
| GVS | Sorption isotherms are obtained using a SMS DVS Intrinsic moisture sorption analyser, controlled by SMS Analysis Suite software. The sample temperature is maintained at 25° C. by the instrument controls. The humidity is controlled by mixing streams of dry and wet nitrogen, with a total flow rate of 200 mL/min. The relative humidity is measured by a calibrated Rotronic probe (dynamic range of 0.1-100% % RH), located near the sample. The weight change, (mass relaxation) of the sample as a function of % RH is constantly monitored by the microbalance (accuracy ±0.005 mg). Typically 5-20 mg of sample is placed in a pre- tared stainless steel mesh basket under ambient conditions. The sample is loaded and unloaded at 40% RH and 25° C. (typical room conditions). A moisture sorption isotherm is performed as outlined below (2 scans giving 1 complete cycle). The standard isotherm is performed at 25° C. at 10% RH intervals over a 0.5-90% RH range. |
| Polarised Light Microscopy (PLM) | Samples are studied on a Leica DLM polarised light microscope with a digital video camera for image capture. A small amount of each sample is placed on a glass slide, mounted in immersion oil and covered with a glass slip, the individual particles being separated as well as possible. The sample is viewed with appropriate magnification and partially polarised light, coupled to a λ false-colour filter. |
| DSC | Perkin Elmer DSC 7. Closed Au crucibles, heating rate: 10 or 20° C./min, range: −50° C. to 250° C., or DSC data are collected on a Mettler DSC 823e equipped with a 34 position auto-sampler. The instrument is calibrated for energy and temperature using certified indium. Typically 0.5-3 mg of each sample, in a pin-holed aluminium pan, is heated at 10° C./min from 25° C. to 300° C. A nitrogen purge at 50 mL/min is maintained over the sample. The instrument control and data analysis software is STARe v9.10. |
| FT-IR | Data are collected on a Nicolet Avatar FT-IR spectrometer with a Smart DurasamplIR accessory and controlled by Omnic software. |
| NMR | $^1$H and $^{13}$C Spectra are obtained using a Varian Unity Inova 400 NMR spectrometer with a 5 mm inverse triple resonance probe operating at 400.12 MHz for proton. Samples are prepared in d$_6$-DMSO, unless otherwise stated. Inverse gated $^{13}$C NMR spectra are obtained using a Bruker DPX300 spectrometer using a dual $^1$H/$^{13}$C probe operating at 75.46 MHz for carbon. The sample is prepared by dissolving ~50 mg of material in d$_6$-DMSO. A D1 of thirty seconds is employed with 7168 scans. |
| SS-NMR | $^{13}$C Solid-state NMR spectra are recorded using a Varian VNMRS spectrometer operating at 100.56 MHz for $^{13}$C and with a 6 mm (outside diameter) magic-angle spinning (MAS) probe. They are obtained using cross polarisation and MAS with a 30 seconds recycle delay, 1 millisecond contact time and at a sample spin-rate of 6.8 kHz. Spectral referencing is with respect to an external sample of neat tetramethylsilane, carried out by setting the high-frequency line from adamantane to 38.5 ppm. Measurements are carried out in air and at ambient probe temperature (~25° C.). The samples are analysed as-received. |
| Particle Size distribution (PSD) Laser diffraction | PSD was determined using a Sympatec laser diffraction HELOS/BF particle size instrument fitted with RODOS/ASPIROS dry dispersion unit operating at 2.5 Bar with a sled speed of 25 mm/s, a combination of R1 0.1/0.18 μm-35 μm and R3 0.5/0.9 μm-175 μm lenses were used for the determination. Trigger conditions: 1 ms, 0.2%. |
| XRPD | Bruker D2 Phaser X-Ray Powder Diffraction patterns are collected on a Bruker AXS D2 diffractometer using Cu K radiation (30 kV, 10 mA), θ-θ geometry, using a Lynxeye detector form 5-42 2θ. The software used for data collection is DIFFRAC.SUITE and the data are analysed and presented using Diffrac Plus EVA v 13.0.0.2. Data collection: Angular range: 5 to 42 °2θ; Step size: 0.012 °2θ; Collection time: 0.15 seconds per step. Sample Preparation: Samples run under ambient conditions are prepared as flat plate specimens using powder as received without grinding. Approximately 1-2 mg of the sample is lightly pressed on a silicon wafer to obtain a flat surface. |

Synthetic Preparation of the Salt of the Invention

Example 1

Preparation of Compound 1

1.1. Route 1

1.1.1. 4-[4-(4,4,5,5-Tetramethyl-[1,3,2]dioxaborolan-2-yl)-benzyl]-thiomorpholine-1,1-dioxide

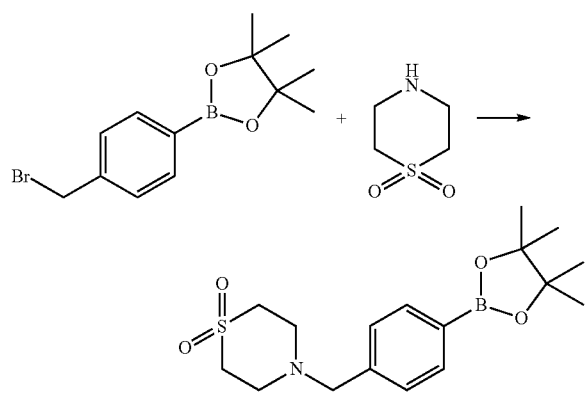

2-(4-Bromomethyl-phenyl)-4,4,5,5-tetramethyl-[1,3,2]dioxaborolane (1 eq) and DIPEA (2 eq) are dissolved in DCM/MeOH (5:1 v:v) under $N_2$ and thiomorpholine 1,1-dioxide (2 eq) is added portionwise. The resulting solution is stirred at room temperature for 16 h. After this time, the reaction is complete. The solvent is evaporated. The compound is extracted with EtOAc and water, washed with brine and dried over anhydrous $MgSO_4$. Organic layers are filtered and evaporated. The final compound is isolated without further purification.

1.1.2. Cyclopropanecarboxylic acid (5-bromo-[1,2,4]triazolo[1,5-a]pyridin-2-yl)-amide

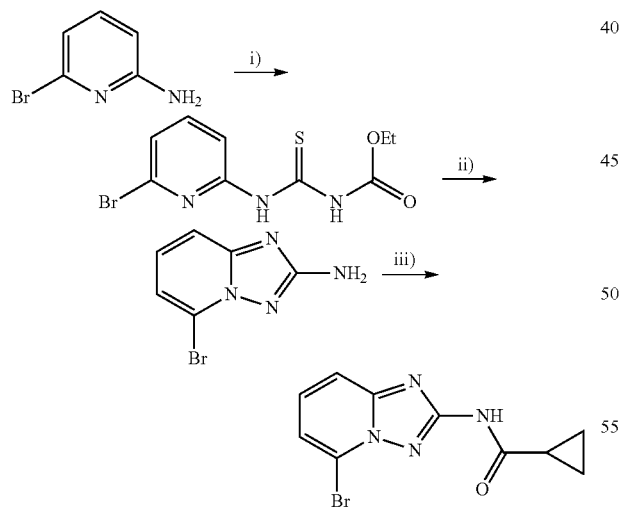

1.1.2.1. Step i): 1-(6-Bromo-pyridin-2-yl)-3-carboethoxy-thiourea

To a solution of 2-amino-6-bromopyridine (1) (253.8 g, 1.467 mol) in DCM (2.5 L) cooled to 5° C. is added ethoxycarbonyl isothiocyanate (173.0 mL, 1.467 mol) dropwise over 15 min. The reaction mixture is then allowed to warm to room temp. (20° C.) and stirred for 16 h. Evaporation in vacuo gives a solid which may be collected by filtration, thoroughly washed with petrol (3×600 mL) and air-dried to afford the desired product. The thiourea may be used as such for the next step without any purification. $^1H$ (400 MHz, $CDCl_3$) δ 12.03 (1H, br s), 8.81 (1H, d), 8.15 (1H, br s), 7.60 (1H, t), 7.32 (1H, dd), 4.31 (2H, q), 1.35 (3H, t).

1.1.2.2. Step ii): 5-Bromo-[1,2,4]triazolo[1,5-a]pyridin-2-ylamine

To a suspension of hydroxylamine hydrochloride (101.8 g, 1.465 mol) in EtOH/MeOH (1:1, 900 mL) is added N,N-diisopropylethylamine (145.3 mL, 0.879 mol) and the mixture is stirred at room temp. (20° C.) for 1 h. 1-(6-Bromo-pyridin-2-yl)-3-carboethoxy-thiourea (2) (89.0 g, 0.293 mol) is then added and the mixture slowly heated to reflux (Note: bleach scrubber is required to quench $H_2S$ evolved). After 3 h at reflux, the mixture is allowed to cool and filtered to collect the precipitated solid. Further product is collected by evaporation in vacuo of the filtrate, addition of $H_2O$ (250 mL) and filtration. The combined solids are washed successively with $H_2O$ (250 mL), EtOH/MeOH (1:1, 250 mL) and $Et_2O$ (250 mL) then dried in vacuo to afford the triazolopyridine derivative (3) as a solid. The compound may be used as such for the next step without any purification. $^1H$ (400 MHz, DMSO-$d_6$) δ 7.43-7.34 (2H, m, 2× aromatic-H), 7.24 (1H, dd, J 6.8 and 1.8 Hz, aromatic-H), 6.30 (2H, br, $NH_2$); m/z 213/215 (1:1, M+H$^+$, 100%).

1.1.2.3. Step iii): Cyclopropanecarboxylic acid (5-bromo-[1,2,4]triazolo[1,5-a]pyridin-2-yl)-amide To a solution of the 2-amino-triazolopyridine obtained in the previous step (7.10 g, 33.3 mmol) in dry MeCN (150 mL) at 5° C. is added $Et_3N$ (11.6 mL, 83.3 mmol) followed by cyclopropanecarbonyl chloride (83.3 mmol). The reaction mixture is then allowed to warm to ambient temperature and stirred until all starting material is consumed. If required, further $Et_3N$ (4.64 mL, 33.3 mmol) and cyclopropanecarbonyl chloride (33.3 mmol) is added to ensure complete reaction. Following solvent evaporation in vacuo the resultant residue is treated with 7 N methanolic ammonia solution (50 mL) and stirred at ambient temp. (for 1-16 h) to hydrolyse any bis-acylated product. Product isolation is made by removal of volatiles in vacuo followed by trituration with $Et_2O$ (50 mL). The solids are collected by filtration, washed with $H_2O$ (2×50 mL), acetone (50 mL) and $Et_2O$ (50 mL), then dried in vacuo to give the desired compound.

1.1.3. Compound 1

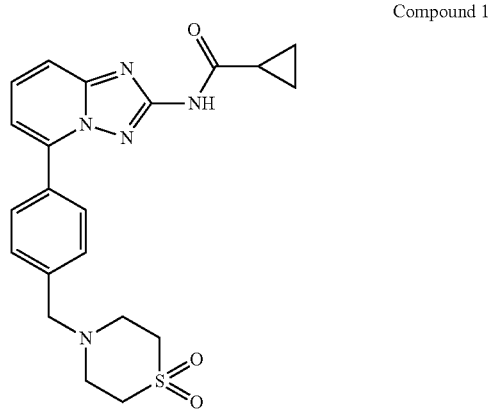 [SMILES: O=C(Nc1nc2cccc(-c3ccc(CN4CCS(=O)(=O)CC4)cc3)n2n1)C1CC1]

Compound 1

4-[4-(4,4,5,5-Tetramethyl-[1,3,2]dioxaborolan-2-yl)-benzyl]-thiomorpholine-1,1-dioxide (1.1 eq.) is added to a solution of cyclopropanecarboxylic acid (5-bromo-[1,2,4]triazolo[1,5-a]pyridin-2-yl)-amide in 1,4-dioxane/water (4:1). K₂CO₃ (2 eq.) and PdCl₂ dppf (0.03 eq.) are added to the solution. The resulting mixture is then heated in an oil bath at 90° C. for 16 h under N₂. Water is added and the solution is extracted with ethyl acetate. The organic layers are dried over anhydrous MgSO₄ and evaporated in vacuo.

The final compound is obtained after purification by flash chromatography.

Alternatively, after completion of the reaction, a palladium scavenger such as 1,2-bis(diphenylphosphino)ethane, is added, the reaction mixture is allowed to cool down and a filtration is performed. The filter cake is reslurried in a suitable solvent (e.g. acetone), the solid is separated by filtration, washed with more acetone, and dried. The resulting solid is resuspended in water, aqueous HCl is added, and after stirring at room temperature, the resulting solution is filtered on celite (Celpure P300). Aqueous NaOH is then added to the filtrate, and the resulting suspension is stirred at room temperature, the solid is separated by filtration, washed with water and dried by suction. Finally the cake is re-solubilised in a mixture of THF/H₂O, treated with a palladium scavenger (e.g. SMOPEX 234) at 50° C., the suspension is filtered, the organic solvents are removed by evaporation, and the resulting slurry is washed with water and methanol, dried and sieved, to obtain the desired compound as a free base.

1.2. Route 2

1.2.1. Step 1: cyclopropanecarboxylic acid [5-(4-hydroxymethyl-phenyl)-[1,2,4]triazolo[1,5-a]pyridin-2-yl]-amide

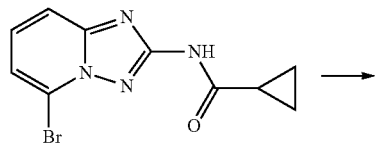

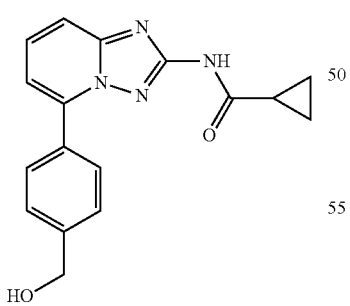

4-(Hydroxymethyl)phenylboronic acid (1.1 eq.) is added to a solution of cyclopropanecarboxylic acid (5-bromo-[1,2,4]triazolo[1,5-a]pyridin-2-yl)-amide in 1,4-dioxane/water (4:1). K₂CO₃ (2 eq.) and PdCl₂ dppf (0.03 eq.) are added to the solution. The resulting mixture is then heated in an oil bath at 90° C. for 16 h under N₂. Water is added and the solution is extracted with ethyl acetate. The organic layers are dried over anhydrous MgSO₄ and evaporated in vacuo. The resulting mixture is used without further purification.

1.2.2. Step 2: Cyclopropanecarboxylic acid [5-(4-bromomethyl-phenyl)-[1,2,4]triazolo[1,5-a]pyridin-2-yl]-amide

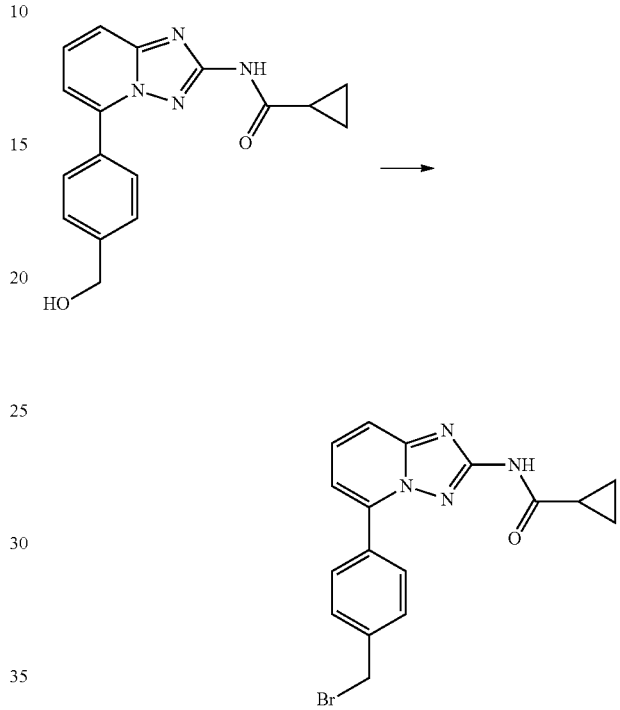

To a solution of cyclopropanecarboxylic acid [5-(4-hydroxymethyl-phenyl)-[1,2,4]triazolo[1,5-a]pyridin-2-yl]-amide (1.0 eq) in chloroform is slowly added phosphorus tribromide (1.0 eq.). The reaction mixture is stirred at room temperature for 20 h, quenched with ice and water (20 mL) and extracted with dichloromethane. The organic layer is dried over anhydrous MgSO₄, filtered and concentrated to dryness. The resulting white residue is triturated in dichloromethane/diethyl ether 2:1 to afford the desired product.

Step 3

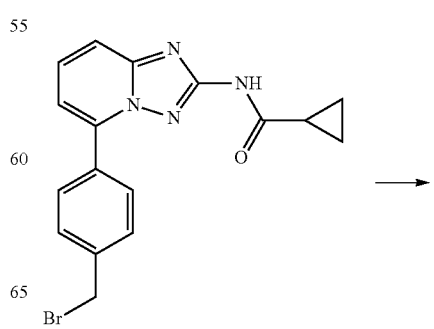

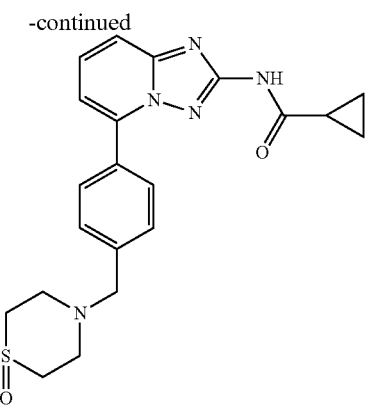

Cyclopropanecarboxylic acid [5-(4-bromomethyl-phenyl)-[1,2,4]triazolo[1,5-a]pyridin-2-yl]-amide (1 eq) and DIPEA (2 eq) are dissolved in DCM/MeOH (5:1 v:v) under $N_2$ and thiomorpholine 1,1-dioxide (1.1 eq) is added dropwise. The resulting solution is stirred at room temperature for 16 h. After this time, the reaction is complete. The solvent is evaporated. The compound is dissolved in DCM, washed with water and dried over anhydrous $MgSO_4$. Organic layers are filtered and evaporated. The final compound is isolated by column chromatography using EtOAc to afford the desired product.

Example 2

Preparation of the Salts of Compound 1

2.1. Protocol 1

Solvent is added to samples of Compound 1 (approximately 5 mg) in relative volume portions of 10, 15 and 20 volumes, and after each addition the samples are agitated at 50° C. in a shaker for 20 min to encourage dissolution, before cooling to room temperature for the next addition of solvent. The solvent is selected from isopropanol, ethanol, methanol, isopropyl acetate, THF, TBME, acetone, methyl ethyl ketone, DCM, and MeCN.

Under these conditions, almost full dissolution of Compound 1 only occurs in DCM.

After addition of 20 relative volumes of solvent, HCl (1 M solution in THF) (12 μL~1 eq.) is added to each sample and observations are made. The samples are stored in a shaker on a heat cool cycle (50° C./room temperature, 4 h at each temperature) for 16 h. The resultant solids are isolated by vacuum filtration, dried under suction and analysed by XRPD.

HCl salt formation is only observed in ethanol, methanol, THF, acetone, methyl ethyl ketone, and MeCN.

2.2. Protocol 2

Compound 1 (~20 mg) is treated with 400 μL (20 volumes) of solvent (THF, acetone) and treated with aqueous acid solutions at room temperature (see Table III below). The experiments are placed in a maturation chamber which is cycled between ambient temperature and 50° C. with four h spent under each condition. After three days solids are isolated by filtration and any solutions are allowed to evaporate. Any further solids formed are isolated, or remaining oils are treated with EtOAc and placed back in the maturation chamber for four days. Any further solids are isolated by filtration. The solids are analysed by XRPD.

When subjected to this protocol, salts are only formed in sulfuric acid, pTSA, 1,2-ethane disulfonic acid, 2-hydroxyethanesulfonic acid, naphthalene 2-sulfonic acid, and maleic acid.

TABLE III

Acids used in Protocol 2

| Acid | Solvent | Eq. Acid |
|---|---|---|
| 1-5-Naphthalene disulfonic acid | Water | 2.1 |
| sulfuric acid | Water | 2.1 |
| 1-2-Ethane disulfonic acid | Water | 2.1 |
| p-Toluene sulfonic acid | Water | 2.1 |
| Methane sulfonic acid | Water | 2.1 |
| 1-5-Naphthalene disulfonic acid | Water | 1.1 |
| sulfuric acid | Water | 1.1 |
| 1-2-Ethane disulfonic acid | Water | 1.1 |
| p-Toluene sulfonic acid | Water | 1.1 |
| Methane sulfonic acid | Water | 1.1 |
| Naphthalene-2-sulfonic acid | Water | 1.1 |
| Benzene sulfonic acid | Water | 1.1 |
| Oxalic acid | Water | 1.1 |
| 2-Hydroxy ethanesulfonic acid | Water | 1.1 |
| Maleic acid | Water | 1.1 |
| Phosphoric acid | Water | 1.1 |
| Ethane sulfonic acid | Water | 1.1 |
| Malonic acid | Water | 1.1 |
| 2-5-Dihydroxybenzoic acid | THF | 1.1 |
| L-Tartaric acid | Water | 1.1 |

2.3. Protocol 3

To a suspension of Compound 1 (~25 mg) and solvent (MeOH, THF, Acetone, or DCM) (20 relative volumes) at approximately 40° C. is added 1.05 or 2.1 eq. of the acid (HCl, HBr, $H_2SO_4$, Ph-$SO_3$H, oxalic acid, maleic acid, or pTSA.$H_2$O), and visual observations are made. The samples are stored in a shaker at 26° C. for 14 h. An aliquot is taken and the solid is isolated by vacuum filtration, dried under suction and analysed by XRPD. The mixtures are then stored in a shaker at 26° C. for a further 31 h. The remaining solid from those samples exhibiting crystalline XRPD patterns different to the free base are isolated by vacuum filtration and further analysis is done (DSC, NMR, Stability).

The remainder of each sample is stored in a shaker on a heat/cool cycle (50° C./room temperature, 4 h at each temperature) for 136 h. Again, an aliquot of each sample is taken and the solid is isolated by vacuum filtration, dried under suction and analysed by XRPD. The remaining solid from those samples exhibiting crystalline XRPD patterns different to the free base is isolated by vacuum filtration and further analysis is undertaken (DSC, NMR, Stability).

Samples that remain in solution are allowed to slowly evaporate under ambient conditions until the solvent has evaporated, and any solid formed is isolated and analysed by XRPD.

When subjected to this protocol, salts are only formed in HBr, HCl, sulfuric acid, pTSA, and maleic acid.

2.4. Protocol 4

2.4.1. HCl

HCl (1 M solution in THF) (655 μL, 0.65 mmol, 1.1 eq.) is added to a stirred suspension of Compound 1 (252.6 mg, 0.59 mmol, 1 eq.) and methanol (5.05 mL, 20 vols) at 50° C. The mixture is cooled to 25° C. at 1° C./min and stirred at 25° C. for 22 h.

The solid is isolated by vacuum filtration and dried under suction.

The XRPD analysis confirmed the formation of a stable non-hygroscopic salt, containing 4-5% water, having an aqueous solubility measured at 1.9 mg/mL.

2.4.2. Maleic Acid

Compound 1 (246.4 mg, 0.58 mmol, 1 eq.) is suspended in 5% water in acetone (4.95 mL, 20 vols) at 25° C. and the sample is warmed to 50° C. Maleic acid (1 M solution in THF) (1.2 mL, 1.22 mmol, 2.1 eq.) is added to the stirred suspension at 50° C. The mixture is cooled to 25° C. at 1° C./min and stirred at 25° C. for 22 h.

The solid was isolated by vacuum filtration and dried under suction.

The XRPD analysis confirmed the formation of the formation of a stable non-hygroscopic salt, having an aqueous solubility measured at 0.4 mg/mL.

2.4.3. pTSA pTSA (1 M solution in EtOH) (1.3 mL, 1.3 mmol, 2.2 eq.) is added to a stirred suspension of Compound 1 (250.7 mg, 0.59 mmol, 1 eq.) and THF (5 mL, 20 vols) at 50° C. The mixture is cooled to 25° C. at 1° C./min and stirred at 25° C. for 22 h.

The solid is isolated by vacuum filtration and dried under suction.

The XRPD analysis confirmed the formation of a salt, which appeared to be unstable.

2.5. Complementary Salt Analysis

The solids recovered from this protocol are also subjected to purity, salt equivalent (IC), NMR (residual solvent), DSC, TGA (solvates), and stability evaluation (1 week at 40° C./75% Relative humidity).

2.5.1. pKa Determination

Data are collected on a Sirius GlpKa instrument with a D-PAS attachment. Measurements are made at 25° C. in aqueous solution by UV and in methanol water mixtures by potentiometry. The titration media was ionic-strength adjusted with 0.15 M KCl (aq). The values found in the methanol water mixtures are corrected to 0% co-solvent via a Yasuda-Shedlovsky extrapolation.

The data are refined using Refinement Pro software.

Following this procedure, the following values are obtained: 1.58±0.01, 3.68±0.02, and 12.02±0.01.

2.5.2. pH Determination

The pH measurements are performed on the test material as a slurry. Typically 1 mL of demineralized water is added to about 300 mg of the tested material and the suspension is then vortexed. If insufficient liquid is available or viscosity is too high for measurement of pH using a pH electrode, the amount of water is increased until a measurement is possible in increments of 1 ml. The pH electrode was calibrated using a three point calibration.

Finally, pH is recorded at start (=after 2 min to allow a relatively stable measurement of the pH).

2.5.3. Solubility Study

2.5.3.1. Protocol

The solubility of a compound is determined in different solvents by equilibrating an excess of product for at least 24 h at 20° C. on a rotary shaker. The supersaturated solution is then filtered and the concentration of product in the filtrate is determined using UV-spectrometry.

In water, the influence of the pH is adjusted to pH 2, pH 7, and pH 9. HCl and NaOH are used to adjust the pH.

2.5.3.2. Results

For example, when subjected to this protocol, the solubility of the free base and the corresponding HCl salt measurement are reported in Table IV below. Unexpectedly, going from Compound 1 to Compound 1.HCl.3H$_2$O does not systematically result in an improved solubility.

TABLE IV

Solubility of Compound 1 as a free base and the corresponding HCl salt in various solvents

| Solvent | Compound 1 Solubility (mg/mL) | Compound1•HCl•3H$_2$O Solubility (mg/mL) |
|---|---|---|
| Acetone | 0.420 | 0.415 |
| Acetonitrile | 0.605 | 7.36 |
| Acetonitrile/water (1/1) | 1.57 | 25.6 |
| Acetonitrile/water (4/1) | 3.11 | 7.81 |
| Dichloromethane | 5.66 | 0.388 |
| Ethanol | 0.151 | 0.764 |
| 0.005M HCl | 0.252 | 3.10 |
| 0.01M HCl | 0.288 | 2.34 |
| 0.01M HCl + 2.0% Tween 80 | 0.313 | 2.79 |
| HP-β-CD 40% pH 2 | 0.577 | 7.88 |
| HP-β-CD 40% pH 3 | 0.550 | 9.33 |
| HP-β-CD 40% pH 4 | 0.520 | 2.79 |
| Methanol | 0.432 | 0.743 |
| PEG400 | 1.53 | 36.6 |
| Propanol | 0.134 | 0.663 |
| Propylene glycol | 0.464 | 11.7 |
| t-butyl methyl ether | <0.00239 | 0.0263 |
| Tetrahydrofuran | 0.740 | 0.208 |
| Water (purified) | 0.00384 | 3.17 |
| Water pH 2 | 0.291 | 8.05 |
| Water pH 7 | 0.00432 | 2.26 |
| Water pH 9 | 0.00429 | 2.68 |
| Water/ethanol 1/1 | 0.327 | 8.68 |

2.5.4. Conclusions

As demonstrated above, the solubility of Compound 1 varies greatly depending on the solvent used, and salt formation does not inevitably occurs with every acid, illustrating the difficulty in selecting a satisfactory combination of solvent and acid, which is specific to Compound 1.

Example 3

Polymorphism Study

3.1. Compound 1

3.1.1. Amorphous Compound 1 Formation

Compound 1 (38 mg) is heated in a DSC instrument under nitrogen according to the following procedure: 1) Heated from 30° C. to 250° C. at 10° C./min; 2) Held isothermal for 1 min; 3) Cooled from 250° C. to 30° C. at 100° C./min; and 4) Held isothermal for 4 min.

The resulting solid is confirmed to be amorphous by XRPD analysis.

3.1.2. Polymorphism Study

Amorphous compound was subjected to forty different solvents (ethyl formate, TBME, acetone, methyl acetate, methanol, tetrahydrofuran, diisopropyl ether, ethyl acetate, ethanol, methylethyl ketone, acetonitrile, t-BuOH, 2-Propanol, 1-2-Dimethoxyethane, Isopropyl Acetate, 1-Propanol, 2-Butanol, nitromethane, 1-4-Dioxane, propyl acetate, 2-Pentanone, 2-Methyl-1-Propanol, Toluene, Isobutyl Acetate, Methylisobutyl Ketone, 1-Butanol, 2-Methoxyethanol, Butyl Acetate, Methylbutyl Ketone, 3-Methyl-1-Butanol, 2-Ethoxyethanol, 1-Pentanol, Anisole, Benzonitrile, nitrobenzene, IPA+5% water, EtOH+5% water, MeCN+5% water, THF+5% water, and acetone+5% water) and thermally cycled between ambient and 50° C. with four h spent under each condition. After five days the solids are collected by filtration and initially analysed by XRPD.

3.1.3. Compound 1 Polymorphism Results

When subjected to this protocol, the obtained solids were analysed by XRPD, and the following most stable patterns are reported in the Table V, Table VI, and Table VII below.

TABLE V

Compound 1 Pattern 1 XRPD pattern (Error! Reference source not found.)

| Angle (2θ°) | Intensity (%) |
| --- | --- |
| 16.8 | 100.0 |
| 9.4 | 30.4 |
| 9.6 | 14.0 |
| 13.1 | 26.2 |
| 14.3 | 12.2 |
| 17.3 | 12.4 |
| 18.4 | 9.5 |
| 18.7 | 13.0 |
| 19.0 | 43.8 |
| 20.6 | 9.1 |
| 20.8 | 15.3 |
| 21.3 | 20.5 |
| 23.8 | 18.0 |
| 24.6 | 14.3 |
| 25.2 | 5.8 |
| 29.7 | 8.7 |

TABLE VI

Compound 1 Pattern 3 XRPD pattern (Error! Reference source not found.)

| Angle (2θ°) | Intensity (%) |
| --- | --- |
| 8.6 | 52 |
| 9.7 | 24.6 |
| 10.6 | 35.5 |
| 13.0 | 39.4 |
| 15.3 | 61.7 |
| 16.9 | 40 |
| 17.3 | 45.6 |
| 17.7 | 50.3 |
| 17.9 | 14.1 |
| 18.3 | 10.9 |
| 18.9 | 100 |

TABLE VI-continued

Compound 1 Pattern 3 XRPD pattern (Error! Reference source not found.)

| Angle (2θ°) | Intensity (%) |
| --- | --- |
| 19.3 | 21.4 |
| 19.6 | 12.6 |
| 19.8 | 28.1 |
| 20.0 | 28.7 |
| 20.3 | 13.9 |
| 20.8 | 52.2 |
| 23.0 | 37 |
| 23.5 | 15.4 |
| 23.9 | 50.1 |
| 24.4 | 23.8 |
| 25.0 | 14.1 |
| 29.1 | 15 |
| 33.5 | 32.3 |
| 34.9 | 23.6 |

TABLE VII

Compound 1 Pattern 4 XRPD pattern (Error! Reference source not found.)

| Angle (2θ°) | Intensity (%) |
| --- | --- |
| 7.2 | 100 |
| 8.2 | 56.9 |
| 10.9 | 85 |
| 14.4 | 23.5 |
| 15.3 | 13.3 |
| 16.4 | 26.4 |
| 17.4 | 61.3 |
| 18.4 | 75.7 |
| 18.5 | 89.6 |
| 18.8 | 69.6 |
| 19.2 | 32.3 |
| 19.9 | 58.6 |
| 20.2 | 46.1 |
| 20.5 | 42.9 |
| 21.8 | 18.4 |
| 22.7 | 24.7 |
| 25.4 | 55.2 |
| 27.5 | 47.6 |
| 28.2 | 18.6 |
| 30.7 | 13.9 |
| 32.5 | 16.3 |

3.2. Polymorphism of HCl Salts of Compound 1 and Solvates Thereof

3.2.1. Amorphous HCl Salts of Compound 1 Formation

Compound 1 (25.47 mg) is mixed with water (70 mL, 2750 relative volumes) and stirred at room temperature for 30 min. The mixture is filtered through a 0.45 mm PVDF membrane syringe filter and frozen in a −78° C. bath. The solvent is removed using a freeze drier to yield amorphous Compound 1 mono-HCl salt (confirmed to by XRPD, glass transition at 149° C. (modulated DSC analysis))

3.2.2. Study Protocols

Volumes of 25 different solvents (Acetone, anisole, butanol, butyl acetate, TBME, DMSO, ethanol, ethyl acetate, heptane, isopropyl acetate, MEK, isopropyl acetate, MeCN, cyclohexane, DCM, dioxane, methanol, nitromethane, THF, methyl THF, toluene, water, 10% aqueous acetone, 10% aqueous THF, and 10% methanol), are added to amorphous mono-HCl salt of Compound 1, said volumes ranging from 125 μL (5 rel vol) to 1 mL (40 rel vol), or until a mobile suspension or almost complete dissolution is observed. The sample is stored in a shaker on a heat/cool cycle (50° C./room temperature, 4 h) for 23 h.

After 23 h, where solid has formed, an aliquot is taken and the solid is isolated by vacuum filtration, whereas the remaining suspension is kept in a shaker on a heat/cool cycle (50° C./room temperature, 4 h). The solid from the aliquot is dried under suction for 30 min and analysed by XRPD, then dried further in a vacuum oven at 30° C. and 5 mbar for 34 h and re-analysed by XRPD. Finally, the dried sample is stored at 40° C./75% RH for 72 h and re-analysed by XRPD.

After 47 h, where solid has formed in the suspension, an aliquot is taken and the solid is isolated by vacuum filtration, whereas the remaining suspension is kept in a shaker on a heat/cool cycle (50° C./room temperature, 4 h). The solid from the aliquot is stored under ambient conditions for 72 h and 14 d with analysis by XRPD at each time point. The solid, which has been stored under ambient conditions for 14 d, is stored at 40° C./75% RH for 43 h and re-analysed by XRPD.

After 143 h, where solid has formed, an aliquot is taken from the remaining suspension stored in a shaker on a heat/cool cycle (50° C./room temperature, 4 h) and the solid is isolated by vacuum filtration, dried under suction for 2 h, then analysed by XRPD. The isolated solid is dried in a vacuum oven at 30° C. and 5 mbar for 20 h and re-analysed by XRPD. The dried sample is stored at 40° C./75% RH for 114 h and re-analysed by XRPD.

3.2.3. Results

Further to this study, two stable forms are identified.

3.2.3.1. Compound 1.HCl

HCl (3.6 M solution in dioxane) (2.5 mL, 9.05 mmol 1.1 eq.) is added portion-wise to a stirred suspension of amorphous Compound 1 (3.499 g, 8.22 mmol, 1 eq.) and methanol (70 mL, 20 relative volumes) at 50° C. over a period of 2 min. The mixture is cooled to 20° C. at 0.1° C./min and stirred at 20° C. for a further 10 h. The mixture is cooled to 15° C. at 0.5° C./min and stirred for 30 min. The resultant solid is isolated by vacuum filtration, washed with methanol (2×3.5 mL, 1×7 mL) and dried under suction to yield Compound 1.HCl.

3.2.3.2. Compound 1.HCl.3H$_2$O

HCl (1 M solution in THF) (250 μL, 0.25 mmol, 1.05 eq.) is added to a suspension of amorphous Compound 1 (100.37 mg, 0.24 mmol, 1 eq.) and DCM (2 mL, 20 relative volumes) at 40° C. The mixture is stored in a shaker on a heat/cool cycle (40° C./room temperature, 4 h) for 70 h. The solid is isolated by vacuum filtration and dried under suction to yield Compound 1.HCl.3H$_2$O.

3.2.3.3. Analysis

The X-Ray diffraction patterns are disclosed in Table VIII and Table IX below.

TABLE VIII

Compound 1•HCl XRPD pattern (Error! Reference source not found.)

| Angle (2θ°) | Intensity (%) |
|---|---|
| 7.4 | 100.0 |
| 8.9 | 15.6 |
| 12.4 | 21.3 |
| 14.8 | 61.1 |
| 15.1 | 31.7 |
| 16.9 | 15.9 |
| 17.6 | 27.7 |
| 19.4 | 11.4 |
| 20.7 | 43.4 |
| 21.1 | 11.9 |
| 22.8 | 14.6 |
| 24.9 | 12.3 |
| 26.0 | 12.3 |
| 28.6 | 14.2 |
| 29.8 | 27.3 |
| 32.6 | 10.2 |

TABLE IX

Compound 1•HCl•3H$_2$O XRPD pattern (Error! Reference source not found.)

| Angle (2θ°) | Intensity (%) |
|---|---|
| 7.3 | 61.4 |
| 8.4 | 35.3 |
| 8.8 | 62.8 |
| 10.7 | 26.3 |
| 12.0 | 22.5 |
| 12.2 | 18.1 |
| 13.2 | 23.6 |
| 13.7 | 16.1 |
| 14.5 | 14.0 |
| 16.3 | 31.0 |
| 16.7 | 100.0 |
| 17.6 | 11.3 |
| 19.3 | 20.8 |
| 20.2 | 87.5 |
| 20.6 | 16.4 |
| 21.0 | 18.0 |
| 21.4 | 52.0 |
| 21.8 | 58.8 |
| 22.8 | 45.0 |
| 23.4 | 57.5 |
| 23.9 | 10.6 |
| 24.5 | 10.8 |
| 25.2 | 21.7 |
| 25.7 | 35.3 |
| 25.9 | 33.1 |
| 26.4 | 11.7 |
| 27.2 | 13.0 |
| 27.7 | 16.6 |
| 28.3 | 10.8 |
| 28.6 | 19.3 |
| 28.9 | 17.2 |
| 29.2 | 20.2 |

TABLE IX-continued

Compound 1•HCl•3H$_2$O XRPD pattern (Error! Reference source not found.)

| Angle (2θ°) | Intensity (%) |
|---|---|
| 29.6 | 47.6 |
| 32.7 | 26.1 |

3.2.3.4. Compound 1.HCl.3H$_2$O Single Crystal X-Ray Diffraction (Error! Reference Source not Found.)

Compound 1.HCl.3H$_2$O is recrystallized from acetone:water (1:1). The results are disclosed in Table X below.

TABLE X

Single Crystal structure of Compound 1•HCl•3H$_2$O

| | | | | | |
|---|---|---|---|---|---|
| Molecular formula | | C$_{21}$H$_{24}$N$_5$O$_3$S•Cl•$_3$(H$_2$O) | | | |
| Molecular weight | | 516.02 | | | |
| Crystal system | | Monoclinic | | | |
| Space group | P2$_{1/n}$ | a | 13.1388(4) Å | α | 102.089(2)° |
| | | b | 8.9437(3) Å | β | |
| | | c | 21.6376(9) Å | γ | |
| V | | 2486.24(15) Å$^3$ | | | |
| Z | | 4 | | | |
| Dc | | 1.379 mg/m$^3$ | | | |
| μ | | 0.284 mm$^{-1}$ | | | |
| Source | | Mo-Kα, 0.71073 Å | | | |
| F(000) | | 1088 | | | |
| T | | 120(2) K | | | |
| Crystal | | colourless prism, 0.39 × 0.16 × 0.12 mm | | | |
| θ range for data collection | | 2.982-27.483° | | | |
| Completeness | | 99.3% | | | |
| Reflections | | 21028 | | | |
| Unique reflections | | 5649 | | | |
| R$_{int}$ | | 0.0307 | | | |

Refinement method is based on Full-matrix least-squares on F$^2$. R[F$^2$>2σ(F$^2$)]=0.0377 and wR(F$^2$)=0.0837. Goodness of fit (S)=1.109. The refinement method used 5649 reflections, 339 parameters and 0 restraints. All hydrogen positions were identified using the difference map and those attached to C atoms & N atoms were then placed in calculated positions and refined using a riding model. Those hydrogen's attached to the water oxygen's and nitrogen were freely refined. The final Δ$_{ρmax}$=0.314 e Å$^{-3}$ and Δ$_{ρmin}$=-0.368 e Å$^{-3}$.

The crystal structure of Compound 1.HCl.3H$_2$O (Error! Reference source not found.) shows the unexpected inclusion of the water molecules in the crystal lattice which may provide further stabilisation of the system.

Example 4

Large Scale Compound 1.HCl.3H$_2$O Formation

4.1. Protocol 1

To Compound 1 (44 kg, 1.0 eq) under inert atmosphere, is added water (15 rel vol, 1000 L), and the mixture is stirred at 50° C. 3.5 eq. aq HCl (5 rel vol) is added over 10-15 min, at a maximum temperature of 55° C. Upon completion of the addition, the stirring is continued at 50° C. for 15 min, and the reaction is then cooled to 15° C. and stirred at that temperature for at least 12 h but no more than 24 h.

The resulting solid is separated by filtration, and the cake is washed with water (2.0 rel vol), and the cake is dried under nitrogen for at least 4 h to afford the desired product.

4.2. Protocol 2

To Compound 1 (45 g, 106 mmol, 1 eq.) under inert atmosphere is added DCM (675 mL) and methanol (225 mL). The resulting suspension is heated to 35° C. under stirring, and trimercaptotriazine trisodium salt 15% in water (22.5 g, 14 mmol, 0.13 eq) is added, and the resulting solution is stirred for 5 h, after which the solution is filtered on 0.45 μm paper under nitrogen pressure.

To the filtrate is added water (50 mL), and the resulting biphasic mixture is stirred at 35° C. for 15 min, after which period the phases are separated, and the organic layer is allowed to cool down to 20° C., and washed twice more with 50 mL water.

The organic layer is cooled down to 15-20° C., then HCl 10% in methanol (42.4 g, 116 mmol, 1.10 eq.) is added over 30 min, causing the precipitation of a solid. The suspension is further stirred at 20° C. for 3 h, then the precipitate is isolated by filtration, the cake is washed with methanol (2×50 mL) to afford the desired compound, which is dried under vacuum at 45° C. for 3 h. The cake is then resuspended in water (220 mL) and stirred for 6 h at 50° C., and then cooled to 15-20° C. The resulting solid is separated by filtration and the cake is washed with water (2×30 mL), and dried at 45° C. for 3 h to afford the desired product.

4.3. Protocol 3

4.3.1. Step 1: Compound 1.HCl.MeOH

To Compound 1 (100 g, 235 mmol, 1 eq.) suspended in DCM (1.5 L), is added MeOH (0.5 L), and the resulting solution is heated to 35° C. Trimercaptotriazine trisodium 85% (8.7 g, 3 mmol, 0.13 eq.) in water (42 mL) is added and the resulting mixture is stirred at 35° C. for at least 5 h. The solution is then filtered on a 0.45 μm paper filter under nitrogen pressure.

To the resulting solution is added water (150 g), stirred at 35° C. for 15 to 30 min, and the biphasic mixture is separated. The organic layer is washed again twice with water (2×150 g).

Finally, a solution of HCl in MeOH (10% w/w) (141 g) is added, and the suspension is stirred at 20° C. for 3 h, and the resulting solid is separated by filtration, the cake is washed with MeOH (2×118 g), dried under vacuum for 3 h at 45° C., to afford Compound 1.HCl.MeOH which is analysed by XRPD. (Table XI).

4.3.2. Step 2: Compound 1.HCl.3H$_2$O

To formic acid (200 g, 1.6 eq) in water (36 g, 0.4 eq.) is added Compound 1.HCl.MeOH (100 g, 1 eq.) obtained in Step 1 above. The resulting mixture is heated to 55° C. under stirring, and the solution is filtered through a 0.45 μm filter cartridge. Formic acid 85% aq (200 g) is added, and the mixture is cooled to 28-32° C. under gentle stirring.

Water (100 g) is then added, followed with Compound 1.HCl.3H$_2$O (1 g) causing the precipitation of Compound 1.HCl.1.5HCO$_2$H, which is analysed by XRPD (Table XII).

Under stirring at 28-32° C., water (2 L) is added portion-wise in 8 portions of 100 mL, 1 portion of 200 mL, and 2 portions of 500 mL.

The resulting suspension is then filtered, the cake is washed with water (2×100 mL) and dried at 30-35° C. to yield Compound 1.HCl.3H$_2$O, which is analysed by XRPD and DSC. (Error! Reference source not found. and Error! Reference source not found.).

TABLE XI

Compound 1•HCl•MeOH XRPD pattern (Error! Reference source not found.)

| Angle (2θ°) | Intensity (%) |
|---|---|
| 7.1 | 100 |
| 14.4 | 37.9 |
| 16.6 | 8.9 |
| 17.3 | 5.1 |
| 18.9 | 4.3 |
| 23.4 | 4.8 |
| 24.8 | 5.1 |
| 29.0 | 10.4 |

TABLE XII

Compound 1•HCl•HCOOH XRPD pattern (Error! Reference source not found.)

| Angle (2θ°) | Intensity (%) |
|---|---|
| 7.1 | 100 |
| 14.4 | 76.4 |
| 14.8 | 17.1 |
| 16.4 | 25.1 |
| 17.4 | 42.8 |
| 18.6 | 20.6 |
| 20.8 | 13.1 |
| 23.4 | 14.1 |
| 24.5 | 16.1 |
| 24.9 | 13.4 |
| 29.0 | 39.8 |

Example 5

Compound 1.HCl.3H$_2$O Stability Study 5.1. Accelerated Stability Study 5.1.1. Protocol Samples of Compound 1.HCl.3H$_2$O are stored under conditions to evaluate chemical stability and physical stability as described in Table XIII.

TABLE XIII

| Stability conditions | |
|---|---|
| Chemical stability conditions | Physical stability conditions |
| 25° C./60% RH/Open recipient | RT/<5% RH/Open recipient |
| 40° C./75% RH/Open recipient | RT/56% RH/Open recipient |
| 50° C./Closed recipient | RT/75% RH/Open recipient |

Samples are taken at TO, then every month up to 3 months, and analysed by FT-IR, DSC, and XRPD.

5.2. Extended Stability Study 5.2.1. Protocol

Samples of test compounds are stored under conditions to evaluate chemical stability and physical stability as described in Table XIV below:

TABLE XIV

| Stability conditions | |
|---|---|
| Model | Temp (° C.)/RH (%)/recipient |
| Cold conditions | 5° C./_/Closed recipient |
| Long term storage | 25° C./60% RH/Open recipient |
| Intermediate conditions | 30° C./65% RH/Open recipient |
| Accelerated conditions | 40° C./75% RH/Open recipient |

Samples are taken at TO, then every month up to 12 months, then at 18, 24 and 36 months; and each aliquots is then analysed by HPLC, Karl-Fisher titration, FT-IR, DSC, and XRPD.

5.3. GVS Analysis Compound 1.HCl.3H$_2$O

GVS analysis is carried out in order to assess the stability of Compound 1.HCl.3H$_2$O and is presented on Error! Reference source not found. The evolution of the material is followed via XPRD at various time points.

No change in form is observed at elevated RH. Compound 1.HCl.3H$_2$O dehydrates to Compound 1.HCl anhydrous upon heating above 60° C. or at less than 10% RH. Rehydration to Compound 1.HCl.3H$_2$O occurs upon cooling to ambient temperature or by exposure to 20% or greater relative humidity.

5.3.1. Conclusions

Surprisingly, Compound 1.HCl.3H$_2$O can be dehydrated to Compound 1.HCl, but converts back to the more stable trihydrate form Compound 1.HCl.3H$_2$O under normal conditions. This could not have been predicted by the skilled person.

BIOLOGICAL EXAMPLES

Example 6

In Vitro Assays 6.1. JAK1 Inhibition Assay

Recombinant human JAK1 catalytic domain (amino acids 850-1154; catalog number 08-144) is purchased from Carna Biosciences. 10 ng of JAK1 is incubated with 12.5 µg polyGT substrate (Sigma catalog number P0275) in kinase reaction buffer (15 mM Tris-HCl pH 7.5, 1 mM DTT, 0.01% Tween-20, 10 mM MgCl$_2$, 2 µM non-radioactive ATP, 0.25 µCi$^{33}$P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 45 min at 30° C., reactions are stopped by adding of 25 µL/well of 150 mM phosphoric acid. All of the terminated kinase reaction is transferred to prewashed (75 mM phosphoric acid) 96 well filter plates (Perkin Elmer catalog number 6005177) using a cell harvester (Perkin Elmer). Plates are washed 6 times with 300 µL per well of a 75 mM phosphoric acid solution and the bottom of the plates is sealed. 40 µL/well of Microscint-20 is added, the top of the plates is sealed and readout is performed using the Topcount (Perkin Elmer). Kinase activity is calculated by subtracting counts per minute (cpm) obtained in the presence of a positive control inhibitor (10 µM staurosporine) from cpm obtained in the presence of vehicle. The ability of a test compound to inhibit this activity is determined as:

Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series are prepared for the compounds enabling the testing of dose-response effects in the JAK1 assay and the calculation of the $IC_{50}$ for each compound. Each compound is routinely tested at concentration of 20 µM followed by a 1/3 serial dilution, 8 points (20 µM-6.67 µM-2.22 µM-740 nM-247 nM-82 nM-27 nM-9 nM) in a final concentration of 1% DMSO. When potency of compound series increased, more dilutions are prepared and/or the top concentration is lowered (e.g. 5 µM, 1 µM).

The following compounds have been tested for their activity against JAK1 and the $IC_{50}$ values, as determined using the assays described herein, are given below in Table XV.

TABLE XV

JAK1 $IC_{50}$ Values of Compounds

| Cpd # | JAK1 $IC_{50}$ (nM) |
|---|---|
| 1 | 47.07, 55.66, 50.1, 48.29 |

6.2. JAK1 Ki Determination Assay

For the determination of Ki, different amounts of compound are mixed with the enzyme and the enzymatic reaction is followed as a function of ATP concentration. The Ki is determined by means of double reciprocal plotting of Km vs compound concentration (Lineweaver-Burk plot). 1 ng of JAK1 (Invitrogen, PV4774) is used in the assay. The substrate is 50 nM Ulight-JAK-1 (Tyr1023) Peptide (Perkin Elmer, TRF0121) The reaction is performed in 25 mM MOPS pH 6.8, 0.01%, 2 mM DTT, 5 mM $MgCl_2$ Brij-35 with varying concentrations of ATP and compound. Phosphorylated substrate is measured using an Eu-labeled anti-phosphotyrosine antibody PT66 (Perkin Elmer, AD0068). Readout is performed on the envision (Perkin Elmer) with excitation at 320 nm and emission followed at 615 nm and 665 nm.

For example, when Compound 1 is tested in this assay, a Ki value of 39 nM is measured.

6.3. JAK2 Inhibition Assay

Recombinant human JAK2 catalytic domain (amino acids 808-1132; catalog number PV4210) is purchased from Invitrogen. 0.025 mU of JAK2 is incubated with 2.5 µg polyGT substrate (Sigma catalog number P0275) in kinase reaction buffer (5 mM MOPS pH 7.5, 9 mM MgAc, 0.3 mM EDTA, 0.06% Brij and 0.6 mM DTT, 1 µM non-radioactive ATP, 0.25 µCi $^{33}$P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 90 min at 30° C., reactions are stopped by adding of 25 µL/well of 150 mM phosphoric acid. All of the terminated kinase reaction is transferred to prewashed (75 mM phosphoric acid) 96 well filter plates (Perkin Elmer catalog number 6005177) using a cell harvester (Perkin Elmer). Plates are washed 6 times with 300 µL per well of a 75 mM phosphoric acid solution and the bottom of the plates is sealed. 40 µL/well of Microscint-20 is added, the top of the plates is sealed and readout is performed using the Topcount (Perkin Elmer). Kinase activity is calculated by subtracting counts per minute (cpm) obtained in the presence of a positive control inhibitor (10 µM staurosporine) from cpm obtained in the presence of vehicle. The ability of a test compound to inhibit this activity is determined as:

Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series are prepared for the compounds enabling the testing of dose-response effects in the JAK2 assay and the calculation of the $IC_{50}$ for each compound. Each compound is routinely tested at concentration of 20 µM followed by a 1/3 serial dilution, 8 points (20 µM-6.67 µM-2.22 µM-740 nM-247 nM-82 nM-27 nM-9 nM) in a final concentration of 1% DMSO. When potency of compound series increased, more dilutions are prepared and/or the top concentration is lowered (e.g. 5 µM, 1 µM).

The following compounds have been tested for their activity against JAK2 and the $IC_{50}$ values, as determined using the assays described herein, are given below in Table XVI.

TABLE XVI

JAK2 $IC_{50}$ Values of Compounds

| Cpd # | JAK2 $IC_{50}$ (nM) |
|---|---|
| 1 | 31.37, 41.16, 55.49, 167.34 |

6.4. JAK2 Kd Determination Assay

JAK2 (Invitrogen, PV4210) is used at a final concentration of 5 nM. The binding experiment is performed in 50 mM Hepes pH 7.5, 0.01% Brij-35, 10 mM $MgCl_2$, 1 mM EGTA using 25 nM kinase tracer 236 (Invitrogen, PV5592) and 2 nM Eu-anti-GST (Invitrogen, PV5594) with varying compound concentrations. Detection of tracer is performed according to the manufacturer's procedure.

For example, when Compound 1 is tested in this assay, a Kd value of 205 nM is measured.

6.5. JAK3 Inhibition Assay

Recombinant human JAK3 catalytic domain (amino acids 781-1124; catalog number PV3855) is purchased from Invitrogen. 0.025 mU of JAK3 is incubated with 2.5 µg polyGT substrate (Sigma catalog number P0275) in kinase reaction buffer (25 mM Tris pH 7.5, 0.5 mM EGTA, 0.5 mM $Na_3VO_4$, 5 mM b-glycerolphosphate, 0.01% Triton X-100, 1 µM non-radioactive ATP, 0.25 µCi 33P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 105 min at 30° C., reactions are stopped by adding of 25 µL/well of 150 mM phosphoric acid. All of the terminated kinase reaction is transferred to prewashed (75 mM phosphoric acid) 96 well filter plates (Perkin Elmer catalog number 6005177) using a cell harvester (Perkin Elmer). Plates are washed 6 times with 300 µL per well of a 75 mM phosphoric acid solution and the bottom of the plates is sealed. 40 µL/well of Microscint-20 is added, the top of the plates is sealed and readout is performed using the Topcount (Perkin Elmer). Kinase activity is calculated by subtracting counts per minute (cpm) obtained in the presence of a positive control inhibitor (10 µM staurosporine) from cpm obtained in the presence of vehicle. The ability of a test compound to inhibit this activity is determined as:

> Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series are prepared for the compounds enabling the testing of dose-response effects in the JAK3 assay and the calculation of the IC50 for each compound. Each compound is routinely tested at concentration of 20 µM followed by a 1/3 serial dilution, 8 points (20 µM-6.67 µM-2.22 µM-740 nM-247 nM-82 nM-27 nM-9 nM) in a final concentration of 1% DMSO. When potency of compound series increased, more dilutions are prepared and/or the top concentration is lowered (e.g. 5 µM, 1 µM).

The following compounds have been tested for their activity against JAK3 and the $IC_{50}$ values, as determined using the assays described herein, are given below in Table XVII.

TABLE XVII

JAK3 $IC_{50}$ Values of Compounds

| Cpd # | JAK3 $IC_{50}$ (nM) |
|---|---|
| 1 | 149.35, 187.3, 189.3, 194.7 |

6.6. JAK3 Ki Determination Assay

For the determination of Ki, different amounts of compound are mixed with the enzyme and the enzymatic reaction is followed as a function of ATP concentration. The Ki is determined by means of double reciprocal plotting of Km vs compound concentration (Lineweaver-Burk plot). JAK3 (Carna Biosciences, 09CBS-0625B) is used at a final concentration of 10 ng/mL. The substrate is Poly(Glu,Tyr) sodium salt (4:1), MW 20 000-50 000 (Sigma, P0275) The reaction is performed in 25 mM Tris pH 7.5, 0.01% Triton X-100, 0.5 mM EGTA, 2.5 mM DTT, 0.5 mM Na3VO4, 5 mM b-glycerolphosphate, 10 mM MgCl2 with varying concentrations of ATP and compound and stopped by addition of 150 mM phosphoric acid. Measurement of incorporated phosphate into the substrate polyGT is done by loading the samples on a filter plate (using a harvester, Perkin Elmer) and subsequent washing. Incorporated 33P in polyGT is measured in a Topcount scintillation counter after addition of scintillation liquid to the filter plates (Perkin Elmer).

For example, when Compound 1 is tested in this assay, a Ki value of 353 nM is measured.

6.7. TYK2 Inhibition Assay

Recombinant human TYK2 catalytic domain (amino acids 871-1187; catalog number 08-147) is purchased from Carna biosciences. 5 ng of TYK2 is incubated with 12.5 µg polyGT substrate (Sigma catalog number P0275) in kinase reaction buffer (25 mM Hepes pH 7.5, 100 mM NaCl, 0.2 mM $Na_3VO_4$, 0.1% NP-40, 0.1 µM non-radioactive ATP, 0.125 µCi $^{33}$P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 90 min at 30° C., reactions are stopped by adding 25 µL/well of 150 mM phosphoric acid. All of the terminated kinase reaction is transferred to prewashed (75 mM phosphoric acid) 96 well filter plates (Perkin Elmer catalog number 6005177) using a cell harvester (Perkin Elmer). Plates are washed 6 times with 300 µL per well of a 75 mM phosphoric acid solution and the bottom of the plates is sealed. 40 µL/well of Microscint-20 is added, the top of the plates is sealed and readout is performed using the Topcount (Perkin Elmer). Kinase activity is calculated by subtracting counts per minute (cpm) obtained in the presence of a positive control inhibitor (10 µM staurosporine) from cpm obtained in the presence of vehicle. The ability of a test compound to inhibit this activity is determined as:

> Percentage inhibition=((cpm determined for sample with test compound present−cpm determined for sample with positive control inhibitor) divided by (cpm determined in the presence of vehicle−cpm determined for sample with positive control inhibitor))*100.

Dose dilution series are prepared for the compounds enabling the testing of dose-response effects in the TYK2 assay and the calculation of the $IC_{50}$ for each compound. Each compound is routinely tested at concentration of 20 µM followed by a 1/3 serial dilution, 8 points (20 µM-6.67 µM-2.22 µM-740 nM-247 nM-82 nM-27 nM-9 nM) in a final concentration of 1% DMSO. When potency of compound series increased, more dilutions are prepared and/or the top concentration is lowered (e.g. 5 µM, 1 µM).

The following compounds have been tested for their activity against TYK2; and the $IC_{50}$ values, as determined using the assays described herein, are given below in Table XVIII.

TABLE XVIII

TYK2 $IC_{50}$ Values of Compounds

| Cpd # | TYK2 $IC_{50}$ (nM) |
|---|---|
| 1 | 72.7, 73.75, 79.07, 86.77 |

6.8. TYK2 Kd Determination Assay

TYK2 (Carna Biosciences, 09CBS-0983D) is used at a final concentration of 5 nM. The binding experiment is performed in 50 mM Hepes pH 7.5, 0.01% Brij-35, 10 mM $MgCl_2$, 1 mM EGTA using 50 nM kinase tracer 236 (Invitrogen, PV5592) and 2 nM Eu-anti-GST (Invitrogen, PV5594) with varying compound concentrations. Detection of tracer is performed according to the manufacturers' procedure.

For example, when Compound 1 is tested in this assay, a Kd value of 376 nM is measured.

Example 7

Cellular Assays

7.1. JAK-STAT signalling assay

HeLa cells are maintained in Dulbecco's Modified Eagle's Medium (DMEM) containing 10% heat inactivated foetal calf serum, 100 U/mL penicillin and 100 µg/mL streptomycin. HeLa cells are used at 70% confluence for transfection. 20,000 cells in 87 µL cell culture medium are transiently transfected with 40 ng pSTAT1(2)-luciferase reporter (Panomics), 8 ng of LacZ reporter as internal control reporter and 52 ng of pBSK using 0.32 μL Jet-PEI (Polyplus) as transfection reagent per well in 96-well plate format. After overnight incubation at 37° C., 10% $CO_2$, transfection medium is removed. 75 μL of DMEM+1.5% heat inactivated fetal calf serum is added. 15 μL compound at 6.7× concentration is added for 60 min and then 10 μL of human OSM (Peprotech) at 33 ng/mL final concentration.

All compounds are tested in duplicate starting from 20 μM followed by a 1/3 serial dilution, 8 doses in total (20 μM-6.6 μM-2.2 μM-740 nM-250 nM-82 nM-27 nM-9 nM) in a final concentration of 0.2% DMSO.

After overnight incubation at 37° C., 10% $CO_2$ cells are lysed in 100 μL lysis buffer/well (PBS, 0.9 mM $CaCl_2$, 0.5 mM $MgCl_2$, 5% Trehalose, 0.025% Tergitol NP9, 0.15% BSA).

40 μL of cell lysate is used to read β-galactosidase activity by adding 180 μL β-Gal solution (30 μL ONPG 4 mg/mL+ 150 μL β-Galactosidase buffer (0.06 M $Na_2HPO_4$, 0.04 M $NaH_2PO_4$, 1 mM $MgCl_2$)) for 20 min. The reaction is stopped by addition of 50 μL $Na_2CO_3$ 1 M. Absorbance is read at 405 nm.

Luciferase activity is measured using 40 μL cell lysate plus 40 μL of Steadylite® as described by the manufacturer (Perkin Elmer), on the Envision (Perkin Elmer).

10 μM of a pan-JAK inhibitor is used as a positive control (100% inhibition). As negative control 0.5% DMSO (0% inhibition) is used. The positive and negative controls are used to calculate z' and 'percent inhibition' (PIN) values.

Percentage inhibition=((fluorescence determined in the presence of vehicle−fluorescence determined for sample with test compound present) divided by (fluorescence determined in the presence of vehicle−fluorescence determined for sample without trigger))*100.

PIN values are plotted for compounds tested in dose-response, $EC_{50}$ values are derived and disclosed in Table XIX below

TABLE XIX

JAK-STAT $EC_{50}$ values

| Cpd # | $EC_{50}$ (nM) |
|---|---|
| 1 | 922.5, 625.6, 987.7, 1767 |

7.2. OSM/IL-1β Signaling Assay

OSM and IL-1β are shown to synergistically upregulate MMP13 levels in the human chondrosarcoma cell line SW1353. The cells are seeded in 96 well plates at 15,000 cells/well in a volume of 120 μL DMEM (Invitrogen) containing 10% (v/v) FBS and 1% penicillin/streptomycin (InVitrogen) incubated at 37° C. 5% $CO_2$. Cells are preincubated with 15 μL of compound in M199 medium with 2% DMSO 1 hr before triggering with 15 μL OSM and IL-1β to reach 25 ng/mL OSM and 1 ng/mL IL-1β, and MMP13 levels are measured in conditioned medium 48 h after triggering. MMP13 activity is measured using an antibody capture activity assay. For this purpose, 384 well plates (NUNC, 460518, MaxiSorb black) are coated with 35 μL of a 1.5 μg/mL anti-human MMP13 antibody (R&D Systems, MAB511) solution for 24 hrs at 4° C. After washing the wells 2 times with PBS+0.05% Tween, the remaining binding sites are blocked with 100 μL 5% non-fat dry milk (Santa Cruz, sc-2325, Blotto) in PBS for 24 hr at 4° C. Next, the wells are washed twice with PBS+0.05% Tween and 35 μL of 1/10 dilution of culture supernatant containing MMP13 in 100-fold diluted blocking buffer is added and incubated for 4 hr at room temperature. Next the wells are washed twice with PBS+ 0.05% Tween followed by MMP13 activation by addition of 35 μL of a 1.5 mM 4-Aminophenylmercuric acetate (APMA) (Sigma, A9563) solution and incubation at 37° C. for 1 hr. The wells are washed again with PBS+0.05% Tween and 35 μL MMP13 substrate (Biomol, P-126, OmniMMP fluorogenic substrate) is added. After incubation for 24 hrs at 37° C. fluorescence of the converted substrate is measured in a Perkin Elmer Wallac EnVision 2102 Multilabel Reader (wavelength excitation: 320 nm, wavelength emission: 405 nm).

Percentage inhibition=((fluorescence determined in the presence of vehicle−fluorescence determined for sample with test compound present) divided by (fluorescence determined in the presence of vehicle−fluorescence determined for sample without trigger))*100.

For example, when Compound 1 is tested in this assay, an $EC_{50}$ value of 2242.5 (±1098.5) nM is measured.

7.3. PBL Proliferation Assay

Human peripheral blood lymphocytes (PBL) are stimulated with IL-2 and proliferation is measured using a BrdU incorporation assay. The PBL are first stimulated for 72 hrs with PHA to induce IL-2 receptor, then they are fasted for 24 hrs to stop cell proliferation followed by IL-2 stimulation for another 72 hrs (including 24 hr BrdU labeling). Cells are preincubated with test compounds 1 h before IL-2 addition. Cells are cultured in RPMI 1640 containing 10% (v/v) FBS.

Example 8

In Vivo Assays

8.1. PK/PD Study

8.1.1. Dog Bioavailability Study

8.1.1.1. Experimental Set Up

The aim of this experiment is to compare the PK in healthy male beagle dogs (3 dogs per group) after a single oral administration of Compound 1 or as Compound 1.HCl.3$H_2$O formulated as capsules of two different strengths (25 and 100 mg).

The dogs are not fasted before dosing, and have free access to water. Every day of the treatment, a half food ration is provided after the T0 blood sampling, 8 to 17 min before treatment, and the second half ration is given just after dosing or 1 h after treatment for period 2. A 3 days washout period is ensured between treatments.

Compound 1 or Compound 1.HCl.3$H_2$O is administered to a target dose of 10 mg/kg in capsules (either 4×25 mg, or 1×100 mg capsule). The capsule composition is described in Table XX below.

TABLE XX 25 and 100 mg capsules composition

| Component | 25 mg capsule | 100 mg capsule |
|---|---|---|
| Compound 1 | 25.325 mg | 101.3 mg |
| Acdisol | 4 mg | 4 mg |
| Aerosil | 1 mg | 1 mg |

TABLE XX-continued 25 and 100 mg capsules composition

| Component | 25 mg capsule | 100 mg capsule |
|---|---|---|
| Avicel | 243.1 mg | 71 mg |
| Magnesium stearate | 1 mg | 1 mg |

The capsules are administered orally with water (5-10 mL), to provide good oesophageal transit. Each animal is checked at least once daily.

Blood is collected from the jugular vein into lithium heparinised tubes at TO (before food administration) and then at 1 h, 2 h, 4 h, 6 h, 8 h, 10 h, and 24 h post treatment.

Plasma is then obtained from blood by centrifugation (2500 g for 10 min at 4° C.), and stored at −20° C. until analysis.

8.1.1.2. Plasma Analysis

Representative aliquots of plasma are diluted with control dog plasma as necessary to ensure the concentrations present are within the range of the calibration curve, and extracted by protein precipitation with 2 volumes of acidified (with 0.1% formic acid) acetonitrile containing deuterated Compound 1 as internal standard (at 150 ng/mL).

After vortex mixing and centrifugation at 4° C., the supernatants are diluted with a 0.5 volume of HPLC grade water in a midi-eppendorf 96-well plate. The plate is sealed and shaken to ensure sample homogeneity prior to analysis. Samples are assayed for Compound 1 by LC-MS/MS using a Waters TQS mass spectrometer, against a series of matrix matched calibration and quality control standards.

The Waters TQS method has a standard curve range of 1.00 ng/mL (lower limit of quantitation for undiluted samples), to maximally 4000 ng/mL for Compound 1.

Pharmacokinetic analysis is performed using WinNonlin™ software version 5.3, using concentrations from individual animals. Non-compartmental analysis is applied to determine the PK parameters ($C_{max}$, $T_{max}$, $AUC_{0-last}$, $t_{1/2}$, etc. . . . )

Concentrations below the limit of detection are set to zero for descriptive statistics and PK parameter calculations.

The actual doses of Compound 1 administered to each dog are used for dose normalisation of PK parameters ($C_{max}$ and AUC). The results are presented in Table XXI below and in Error! Reference source not found.

TABLE XXI

Dog bioavailability study results

| Compound form | Free base | | HCl•trihydrate | |
|---|---|---|---|---|
| Dose (single oral administration) | 4 × 25 mg/kg | 100 mg/kg | 4 × 25 mg/kg | 100 mg/kg |
| Exposure AUC (μg · h/mL) | 10.4 | 11.1 | 33.6 | 21.7 |
| Tmax (h) | 6.0 | 8.0 h | 2.0 | 2.0 |
| Cmax (μg/mL) | 0.894 | 0.797 | 3.05 | 2.63 |
| $T_{1/2}$ (h) | | Range 4.43-8.96 | | |

Compound 1 (as a free base) is taken orally an therefore passes through the HCl containing acidic gastric route, where Compound 1.HCl should be formed. The skilled person would therefore expect to see no difference between the two administered forms.

However, as illustrated in Error! Reference source not found., on average and at the 2 capsule strengths, Compound 1.HCl.3H₂O is more rapidly absorbed, and shows in vivo improved exposure over Compound 1, which may result in lower dosage regimen, and thereby improved patient compliance, and potentially lower toxicity, or drug-drug interaction problems.

Final Remarks

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of salt of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES (CHMP), C. f. (18 Nov. 2004). *Guideline on Clinical Investigation of Medicinal Products indicated for the treatment of Psoriasis.*

Berishaj, M., Gao, S. P., Ahmed, S., Leslie, K., Al-Ahmadie, H., Gerald, W. L., et al. (2007). Stat3 is tyrosine-phosphorylated through the interleukin-6/glycoprotein 130/Janus kinase pathway in breast cancer. *Breast Cancer Research*, 9(3), 1-9.

Constantinescu, S. N., Girardot, M., & Pecquet, C. (2007). Mining for JAK-STAT mutations in cancer. *Trends in Biochemical Sciences*, 33(3), 122-131.

Dolgin, E. (2011). Companies hope for kinase inhibitor JAK-pot. *Nat Rev Drug Discov*, 10(10), 717-8.

Greene, T W; Wuts, P G M; (1991). *Protecting Groups in Organic Synthesis, Second Edition*. New York: Wiley.

Hilfiker, R., Blatter, F., & von Raumer, M. (2006). Relevance of Solid-state Properties. In *Polymorphism: in the Pharmaceutical Industry* (pp. 1-20). Weinheim: WILEY-VCH Verlag GmbH & Co. KGaA.

Ingersoll, K. S., & Cohen, J. (2008). The impact of medication regimen factors on adherence to chronic. *J Behav Med*, 31(3), 213-224.

Kopf, M., Bachmann, M. F., & Marsland, B. J. (2010). Averting inflammation by targeting the cytokine environment. *Nat Rev: Drug Disc*, 9, 703-718.

Lipinski, C. A., Lombardo, F., Dominy, B. W., & Feeney, P. J. (2001). Experimental and computational approaches to estimate. *Advanced Drug Delivery Reviews solubility and permeability in drug discovery and development settings*, 46, 3-26.

Menet, C. J. (2010). Patent No. WO 2010/149769. PCT.

Mullighan, C. G. (2009). JAK mutations in high-risk childhood acute lymphoblastic leukemia. *Proc. Natl. Acad. Sci.*, 106(23), 9414-9418.

Naka, T., Nishimoto, N., & Kishimoto, T. (2002). The paradigm of IL-6: from basic science to medicine. *Arthritis Res*, 4 (suppl 3), S233-S242.

O'Sullivan, L. A., Liongue, C., Lewis, R. S., Stephenson, S. E., & Ward, A. C. (2007). Cytokine receptor signaling through the Jak-Stat-Socs pathway in disease. *Mol Immuno*, 44(10), 2497-506.

O'Dell, J. R. (2004). Therapeutic Strategies for Rheumatoid Arthritis. *N Engl J Med*, 350, 2591-602.

Punwani, N., Scherle, P., Flores, R., Shi, J., Liang, J., Yeleswaram, S., et al. (2012). Preliminary clinical activity of a topical JAK1/2 inhibitor in the treatment of psoriasis. *J Am Acad Dermatol*, 67, 658-64.

Smolen, J. S., & Steiner, G. (2003). Therapeutic strategies for rheumatoid arthritis. *Nat Rev: Drug Disc*, 2, 473-488.

Tam, L., McGlynn, L. M., Traynor, P., Mukherjee, R., Bartlett, J. M., & Edwards, J. (2007). Expression levels of the JAK/STAT pathway in the transition from hormone-sensitive to hormone-refractory prostate cancer. *British Journal of Cancer*, 97, 378-383.

Vainchenker, W., Dusa, A., & Constantinescu, S. N. (2008). JAKs in pathology: Role of Janus kinases in hematopoietic malignancies and immunodeficiencies. *Seminars in Cell & Developmental Biology*, 19, 385-393.

Verstovsek, S. (2009). Therapeutic potential of JAK2 inhibitors. *Hematology Am Soc Hematol Educ Program*, 636-42.

Xiang, Z., Zhao, Y., Mitaksov, V., Fremont, D. H., Kasai, Y., Molitoris, A., et al. (2008). Identification of somatic JAK1 mutations in patients with acute myeloid leukemia. *Blood*, 111, 4809-4812.

Zenz, R., Eferl, R., Florin, L., Hummerich, L., Mehic, D., Scheuch, H., et al. (2005). Psoriasis-like skin disease and arthritis caused by inducible epidermal deletion of Jun proteins. *Nature*, 437(7057), 369-75.

Zhang, Q. (1996). Activation of JAK/STAT proteins involved in signal transduction pathway mediated by receptor for interleukin 2 in malignant T lymphocytes derived from cutaneous anaplastic large T-cell lymphoma and Sezary syndrome. *Proc. Natl. Acad. Sci.*, 93, 9148-9153.

Zikherman, j., & Weiss, A. (2011). Unraveling the functional implications of GWAS: how T cell protein tyrosine phosphatase drives autoimmune disease. *J Clin Invest*, 121(12), 4618-21.

The invention claimed is:

1. A pharmaceutically acceptable salt of a compound according to Formula (I):

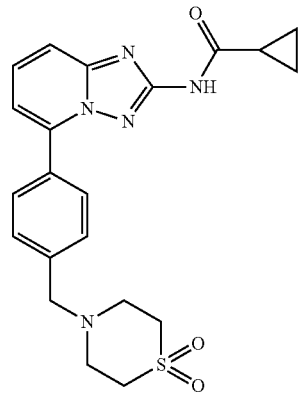

I wherein the salt is a 1:1:3 Free Base/HCl/$H_2O$ adduct and is in a crystalline form, and wherein the 1:1:3 Free Base/HCl/$H_2O$ hydrate of the salt is characterized at least by a powder X-ray diffraction peak at any one or more of the following positions: 7.25, 8.31, 8.78, 10.69, 11.96, 12.25, 13.17, 13.74, 16.23, 16.71, 19.26, 19.64, 20.15, 20.57, 20.95, 21.38, 21.69, 22.77, 23.37, 25.14, 25.71, 25.89, 27.66, 28.57, 28.81, 29.17, 29.58, 30.63, 30.94, 32.06, 32.63, 34.14, 36.22, 36.67, and 37.12° 2θ±0.2° 2θ.

2. A pharmaceutically acceptable hydrate of a salt according to claim 1, wherein the 1:1:3 Free Base/HCl/$H_2O$ hydrate of the salt is characterized by the following diffraction parameters:

| | | |
|---|---|---|
| Molecular formula | $C_{21}H_{24}N_5O_3S \cdot Cl \cdot 3(H_2O)$ | |
| Molecular weight | 516.02 | |
| Crystal system | Monoclinic | |
| Space group | P2$_{1/n}$    a   13.1388(4) Å | α   102.089(2)° |
| | b   8.9437(3) Å | β |
| | c   21.6376(9) Å | γ |
| V | 2486.24(15) Å$^3$ | |
| Z | 4 | |
| Dc | 1.379 mg/m$^3$ | |
| μ | 0.284 mm$^{-1}$ | |
| Source | Mo-Kα, 0.71073 Å | |
| F(000) | 1088 | |
| T | 120(2) K | |
| Crystal | colourless prism, 0.39 × 0.16 × 0.12 mm | |
| θ range for data collection | 2.982-27.483° | |
| Completeness | 99.3% | |
| Reflections | 21028 | |
| Unique reflections | 5649 | |
| R$_{int}$ | 0.0307. | |

* * * * *